US007932390B2

(12) United States Patent
Chen et al.

(10) Patent No.: US 7,932,390 B2
(45) Date of Patent: Apr. 26, 2011

(54) SUBSTITUTED THIENO[3,2-C]PYRIDINE CARBOXYLIC ACID DERIVATIVES

(75) Inventors: Yi Chen, Nutley, NJ (US); Kin-Chun Luk, North Caldwell, NJ (US); Pamela Loreen Rossman, Nutley, NJ (US); Sung-Sau So, Nutley, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 981 days.

(21) Appl. No.: 11/820,306

(22) Filed: Jun. 18, 2007

(65) Prior Publication Data
US 2008/0009515 A1 Jan. 10, 2008

Related U.S. Application Data

(60) Provisional application No. 60/817,616, filed on Jun. 29, 2006.

(51) Int. Cl.
A61K 31/4365 (2006.01)
C07D 515/04 (2006.01)
(52) U.S. Cl. ........................................ 546/114; 514/301
(58) Field of Classification Search .................. 546/114; 514/301
See application file for complete search history.

(56) References Cited

U.S. PATENT DOCUMENTS

| 5,985,853 A | 11/1999 | Laugraud et al. |
| 2001/0020030 A1 | 9/2001 | Stewart et al. |
| 2004/0097485 A1 | 5/2004 | Burkitt et al. |
| 2005/0020619 A1 | 1/2005 | Betschmann et al. |
| 2005/0026944 A1 | 2/2005 | Betschmann et al. |
| 2005/0043347 A1 | 2/2005 | Betschmann et al. |
| 2005/0256154 A1 | 11/2005 | Luke et al. |

FOREIGN PATENT DOCUMENTS

| WO | WO 96/32399 | 10/1996 |
| WO | WO 99/62890 | 12/1999 |
| WO | WO 00/71532 | 11/2000 |
| WO | WO 02/44158 | 6/2002 |
| WO | WO 03/082272 A1 | 10/2003 |
| WO | WO 2004/100947 | 11/2004 |
| WO | WO 2005/056562 | 6/2005 |

OTHER PUBLICATIONS

Blackburn et. al. "Discovery and optimization of N-acyl and N-aroylpyrazolines as B-Raf kinase inhibitors" Bioorganic & Medicinal Chemistry Letters 20 (2010) 4795-4799.*
Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Jiang et. al. "3,5-Disubstituted quinolines as novel c-Jun N-terminal kinase inhibitors." Bioorganic & Medicinal Chemistry Letters 2007, 17, 6378-6382.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Avruch et al., TIBS (19), pp. 279-283 (1994).
Magnuson et al., Cancer Biology, 5, pp. 247-253 (1994).
Sridhar et al., Mol Cancer Ther 2005, 4(4), pp. 677-685 Apr. 2005.
Ansel et. al., Pharmaceutical Dosage Forms and Drug Delivery Systems (6th Ed. 1995) at pp. 456-457.
Ansel et. al., Pharmaceutical Dosage Forms and Drug Delivery Systems (6th Ed. 1995) at pp. 196, 197.
Bollag et al., Current Opinion in Investigational Drugs, 4, vol. 12, pp. 1436-1441 (2003).
Strumberg et al., Onkologie, vol. 28 pp. 101-107 (2005).
Beeram et al., J. Clin. Oncol. vol. 23 pp. 6771-6790 (2005).
Sharma et al., Cancer Research vol. 65 pp. 2412-2421 (2005).
AACR American Association for Cancer Research 93$^{rd}$ Annual Meeting, Apr. 6-10, 2002, San Francisco, California vol. 43, p. 1082.
ASCO 2002 Annual Meeting, Clinical Pharmacology, Preclinical Development of CP-547,632, A Novel VEGFR-2 inhibitor for cancer therapy.
Beebe et al., Cancer Research vol. 63, Nov. 1, 2003, pp. 7301-7309.

* cited by examiner

Primary Examiner — Rita J Desai
Assistant Examiner — David K O'Dell
(74) Attorney, Agent, or Firm — George W. Johnston; Patrica S. Rocha-Tramaloni; Gene J. Yao

(57) ABSTRACT

There are provided compounds of the formula

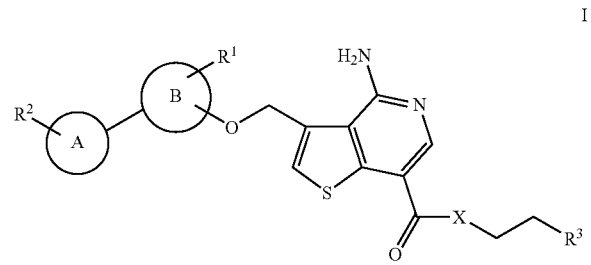

wherein $R^1$, $R^2$, $R^3$, X, ring A and ring B are as described. The compounds exhibit anticancer properties.

11 Claims, No Drawings

SUBSTITUTED THIENO[3,2-C]PYRIDINE CARBOXYLIC ACID DERIVATIVES

PRIORITY TO RELATED APPLICATIONS

This application claims the benefit of U.S. Provisional Application No. 60/817,616, filed Jun. 29, 2006, which is hereby incorporated by reference in its entirety.

BACKGROUND OF THE INVENTION

Many disease states are characterized by uncontrolled proliferation and differentiation of cells. These disease states encompass a variety of cell types and maladies such as cancer, atherosclerosis, and restenosis. In many such disease states kinases, important cellular enzymes that perform essential functions by regulating cell division and proliferation, appear to play a decisive role.

The molecular mechanisms and signaling pathways that regulate cell proliferation and survival are receiving considerable attention as potential targets for anticancer strategies. Recently, there has been a notable increase in efforts directed at targeting the MAPK pathway, which integrates a wide array of proliferative signals initiated by receptor tyrosine kinases (RTKs) and G protein-coupled receptors.

The MAPK signal cascade includes the G protein Ras working upstream of a core module consisting of 3 kinases: Raf phosphorylates and thus activates MEK1/2, which in turn ultimately leads to the activation of ERK1/2. Raf kinase has long been considered an attractive target for drug discovery due to its importance as a potential checkpoint for cancer-related signal transduction (Strumberg and Seeber, Onkologie, 2005, 28: 101-107; Beeram et al., J. Clin. Oncol. 2005, 23: 6771-6790). The importance of the MAPK signalling cascade for the proliferation and survival of tumor cells recently increased with the discovery of activating B-Raf mutations in human tumors. Activating Raf mutations have been identified in melanoma, thyroid, colon, and other cancers (Strumberg and Seeber, Onkologie, 2005, 28: 101-107; Bollag et al., Current Opinion in Investigational Drugs, 2003, 4:1436-1441).

Therefore, in addition to a role in controlling tumors with Ras mutations and activated growth factor receptors, inhibitors of Raf kinase may harbor therapeutic potential in tumors carrying a B-Raf oncogene (Sharma et al., Cancer Res. 2005, 65: 2412-2421).

The mammalian Raf serine/threonine kinase family consists of three 68- to 74-kd proteins termed A-Raf, B-Raf, and C-Raf (Raf-1), which share highly conserved amino-terminal regulatory regions and catalytic domains at the carboxyl terminus. Raf proteins are normally cytosolic but they are recruited to the plasma membrane by the small G-protein Ras, and this is an essential step for their activation by growth factors, cytokines, and hormones. At the membrane, Raf activation occurs through a highly complex process involving conformation changes, binding to other proteins, binding to lipids, and phosphorylation and dephosphorylation of some residues.

A variety of agents have been discovered to interfere with Raf kinase, including antisense oligonucleotides and small molecules. These inhibitors prevent the expression of Raf protein, block Ras/Raf interaction, or obstruct its kinase activity. Down regulation of B-Raf activity by siRNA or through the kinase inhibitor BAY-43-9006 leads to inhibition of the growth of melanoma cells and siRNA-mediated reduction of B-Raf led to decreased tumorigenic potential of 1205 Lu cells. Raf inhibitors that are currently undergoing clinical evaluation show promising signs of anti-cancer efficacy with a very tolerable safety profile. Clinically most advanced is the Raf inhibitor BAY 43-9006, which has recently been approved by the FDA for treatment of metastatic renal cell carcinoma with additional phase III clinical testing for treatment of other cancers.

Despite the progress that has been made, the search continues for low molecular weight compounds that are useful for treating a wide variety of tumors and other proliferative disorders including restenosis, angiogenesis, diabetic retinopathy, psoriasis, surgical adhesions, macular degeneration, and atherosclerosis. Thus, a strong need exists to provide compositions, pharmaceuticals and/or medicaments with anti-proliferative activity. Such compositions, pharmaceuticals and/or medicaments may possess not only strong activity, but also exert diminished side effects in comparison to other anti-proliferative agents. Furthermore, the spectrum of tumors responsive to treatment with such compositions, pharmaceuticals and/or medicaments may be broad. Active ingredients of this type may be suitable in the mentioned indication as single agent, and/or in combination therapy, be it in connection with other therapeutic agents, with radiation, with operative/surgical procedures, heat treatment or any other treatment known in the mentioned indications.

SUMMARY OF THE INVENTION

The present invention relates to substituted thieno[3,2-c]pyridine-7-carboxylic acid derivatives which are small molecule inhibitors of Raf kinase. These compounds are useful as selective anticancer agents.

The present invention provides at least one compound of formula

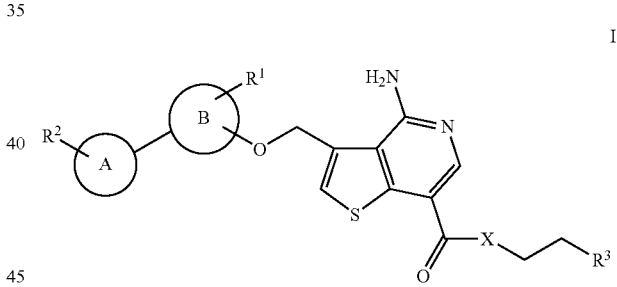

I wherein $R^1$, $R^2$, $R^3$, $R^4$, $R^5$, X, Ring A and Ring B are as described herein.

DETAILED DESCRIPTION OF THE INVENTION

There are provided thieno[3,2-c]pyridine-7-carboxylic acid derivatives of the formula

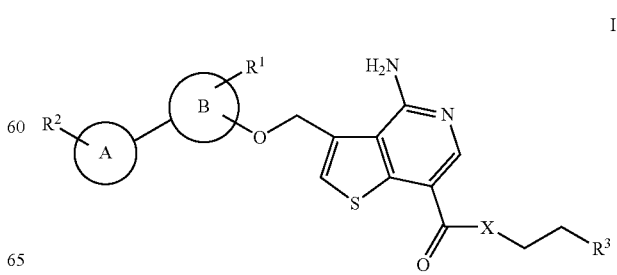

I wherein
R¹ is selected from the group consisting of hydrogen, lower alkyl, lower alkenyl, lower alkynyl, lower alkoxy, cyano, NR⁴R⁵, trifluoromethyl and NO₂;
R² is selected from the group consisting of hydrogen, lower alkyl, substituted lower alkyl, aryl or heteroaryl substituted lower alkyl, lower alkenyl, lower alkynyl, lower alkoxy, aryl, substituted aryl, heteroaryl, substituted heteroaryl, cyano, halogen, methyl sulfonyl, sulfonamide, trifluoromethyl, sulfonyl urea, amide, ester, carbamoyl, carbamate and urea;
R³ is selected from the group consisting of hydrogen, hydroxyl, lower alkyl, substituted lower alkyl, lower alkoxy and NR⁴R⁵;
Ring B is selected from the group consisting of aryl and heteroaryl;
Ring A is optionally further substituted

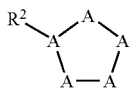

A is independently selected from C, N, O and S and Ring A is aromatic,
R⁴ and R⁵ are selected from hydrogen, lower alkyl or lower alkyl substituted by hydroxyl or lower alkoxy,
X is O or NH,
and the pharmaceutically acceptable salts thereof.
Preferred are compounds of the formula wherein
R¹ is hydrogen or lower alkyl at the C2 of the 5-substituted 1-hydroxy ring B wherein Ring B is phenyl or
R¹ is hydrogen or lower alkyl at the C2 of the 5-substituted 3-hydroxy ring B wherein Ring B is pyridine.
Preferred ring A's include:

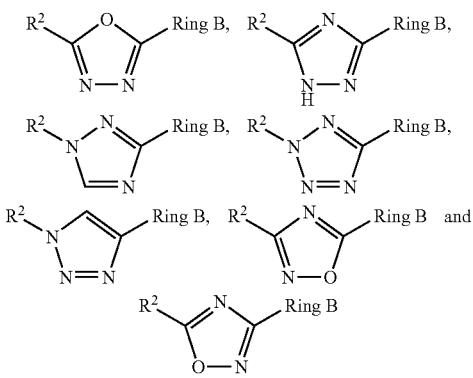

wherein the rings may be further optionally substituted.
Especially preferred are compounds of the formula
4-Chloro-3-[3-(5-methyl-[1,3,4]oxadiazol-2-yl)-phenoxymethyl]-thieno[3,2-c]pyridine-7-carboxylic acid ethyl ester;
4-Amino-3-[3-(5-methyl-[1,3,4]oxadiazol-2-yl)-phenoxymethyl]-thieno[3,2-c]pyridine-7-carboxylic acid ethyl ester;
4-Amino-3-[3-(5-methyl-[1,3,4]oxadiazol-2-yl)-phenoxymethyl]-thieno[3,2-c]pyridine-7-carboxylic acid (2-hydroxy-ethyl)-amide,
4-Chloro-3-[2-methyl-5-(5-methyl-[1,3,4]oxadiazol-2-yl)-phenoxymethyl]-thieno[3,2-c]pyridine-7-carboxylic acid ethyl ester,
4-Amino-3-[2-methyl-5-(5-methyl-[1,3,4]oxadiazol-2-yl)-phenoxymethyl]-thieno[3,2-c]pyridine-7-carboxylic acid ethyl ester,
4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide trifluoro-acetic acid salt,
4-Amino-3-{5-[4-(2-hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide trifluoro-acetic acid salt,
4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide toluene-4-sulfonic acid salt,
4-Chloro-3-[2-methyl-5-(1-methyl-1H-[1,2,3]triazol-4-yl)-phenoxymethyl]-thieno[3,2-c]pyridine-7-carboxylic acid ethyl ester,
4-Amino-3-[2-methyl-5-(1-methyl-1H-[1,2,3]triazol-4-yl)-phenoxymethyl]-thieno[3,2-c]pyridine-7-carboxylic acid ethyl ester,
4-Amino-3-[2-methyl-5-(1-methyl-1H-[1,2,3]triazol-4-yl)-phenoxymethyl]-thieno[3,2-c]pyridine-7-carboxylic acid (2-hydroxy-ethyl)-amide,
4-Chloro-3-{3-[2-(4-methoxy-benzyl)-2H-tetrazol-5-yl]-phenoxymethyl}-thieno[3,2-c]pyridine-7-carboxylic acid ethyl ester,
4-Amino-3-{3-[2-(4-methoxy-benzyl)-2H-tetrazol-5-yl]-phenoxymethyl}-thieno[3,2-c]pyridine-7-carboxylic acid ethyl ester,
4-Amino-3-{3-[2-(4-methoxy-benzyl)-2H-tetrazol-5-yl]-phenoxymethyl}-thieno[3,2-c]pyridine-7-carboxylic acid (2-hydroxy-ethyl)-amide,
4-Chloro-3-[3-(2-methyl-2H-tetrazol-5-yl)-phenoxymethyl]-thieno[3,2-c]pyridine-7-carboxylic acid ethyl ester,
4-Amino-3-[3-(2-methyl-2H-tetrazol-5-yl)-phenoxymethyl]-thieno[3,2-c]pyridine-7-carboxylic acid ethyl ester,
4-Amino-3-[3-(2-methyl-2H-tetrazol-5-yl)-phenoxymethyl]-thieno[3,2-c]pyridine-7-carboxylic acid (2-hydroxy-ethyl)-amide,
4-Chloro-3-{5-[1-(4-chloro-benzyl)-1H-[1,2,3]triazol-4-yl]-2-methyl-phenoxymethyl}-thieno[3,2-c]pyridine-7-carboxylic acid ethyl ester,
4-Amino-3-{5-[1-(4-chloro-benzyl)-1H-[1,2,3]triazol-4-yl]-2-methyl-phenoxymethyl}-thieno[3,2-c]pyridine-7-carboxylic acid ethyl ester,
4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide,
4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide toluene-4-sulfonic acid salt,
4-Chloro-3-{5-[5-(4-chloro-benzyl)-[1,3,4]oxadiazol-2-yl]-2-methyl-phenoxymethyl}-thieno[3,2-c]pyridine-7-carboxylic acid ethyl ester,
4-Amino-3-{5-[5-(4-chloro-benzyl)-[1,3,4]oxadiazol-2-yl]-2-methyl-phenoxymethyl}-thieno[3,2-c]pyridine-7-carboxylic acid ethyl ester,
4-Amino-3-{5-[5-(4-chloro-benzyl)-[1,3,4]oxadiazol-2-yl]-2-methyl-phenoxymethyl}-thieno[3,2-c]pyridine-7-carboxylic acid (2-hydroxy-ethyl)-amide,
4-Chloro-3-{5-[5-(4-chloro-phenyl)-[1,3,4]oxadiazol-2-yl]-2-methyl-phenoxy-methyl}-thieno[3,2-c]pyridine-7-carboxylic acid ethyl ester,
4-Amino-3-{5-[5-(4-chloro-phenyl)-[1,3,4]oxadiazol-2-yl]-2-methyl-phenoxy-methyl}-thieno[3,2-c]pyridine-7-carboxylic acid ethyl ester,
4-Amino-3-{5-[5-(4-chloro-phenyl)-[1,3,4]oxadiazol-2-yl]-2-methyl-phenoxy-methyl}-thieno[3,2-c]pyridine-7-carboxylic acid, 4-Amino-3-{5-[5-(4-chloro-phenyl)-[1,3,4]oxadiazol-2-yl]-2-methyl-phenoxy-methyl}-thieno[3,2-c]pyridine-7-carboxylic acid (2-hydroxy-ethyl)-amide trifluoroacetic acid salt,
4-Chloro-3-[2-methyl-5-(3-methyl-[1,2,4]oxadiazol-5-yl)-phenoxymethyl]-thieno[3,2-c]pyridine-7-carboxylic acid ethyl este,
4-Amino-3-[2-methyl-5-(3-methyl-[1,2,4]oxadiazol-5-yl)-phenoxymethyl]-thieno[3,2-c]pyridine-7-carboxylic acid ethyl ester,
4-Amino-3-[2-methyl-5-(3-methyl-[1,2,4]oxadiazol-5-yl)-phenoxymethyl]-thieno[3,2-c]pyridine-7-carboxylic acid,
4-Amino-3-[2-methyl-5-(3-methyl-[1,2,4]oxadiazol-5-yl)-phenoxymethyl]-thieno-[3,2-c]pyridine-7-carboxylic acid (2-hydroxy-ethyl)-amide trifluoroacetic acid salt,
4-Chloro-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester,
4-Amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester,
4-Amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid (2-hydroxy-ethyl)-amide,
4-Chloro-3-[2-methyl-5-(methyl-4H-[1,2,4]triazol-3-yl)-phenoxymethyl]-thieno[3,2-c]pyridine-7-carboxylic acid ethyl ester,
4-Amino-3-[2-methyl-5-(5-methyl-4H-[1,2,4]triazol-3-yl)-phenoxymethyl]-thieno[3,2-c]pyridine-7-carboxylic acid ethyl ester and
4-Amino-3-[2-methyl-5-(5-methyl-4H-[1,2,4]triazol-3-yl)-phenoxymethyl]-thieno[3,2-c]pyridine-7-carboxylic acid (2-hydroxy-ethyl)-amide.

In the specification, where indicated, the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-2-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the alkyl, aryl, heteroaryl and heterocycle rings are halogen, lower alkoxy, lower alkyl and amino.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

The term "amide" refers to a chemical group that comprises the following functional group: $-C(O)-N-R^aR^b$, wherein $R^a$ and $R^b$ are independently hydrogen or lower alkyl. An example of an amide group is carbamoyl: $-C(O)-NH_2$.

The term "ester" refers to a chemical group that comprises the following functional group $-C(O)-O-R^c$, wherein $R^c$ is an alkyl having from 1 to 6 carbon atoms.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456—The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or sturctural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compounds of formulas I-IV and are cleaved in vivo (in the organism) to the corresponding active carboxylic acid or alcohol respectively.

Compounds of this invention can be synthesized according to the following general schemes.

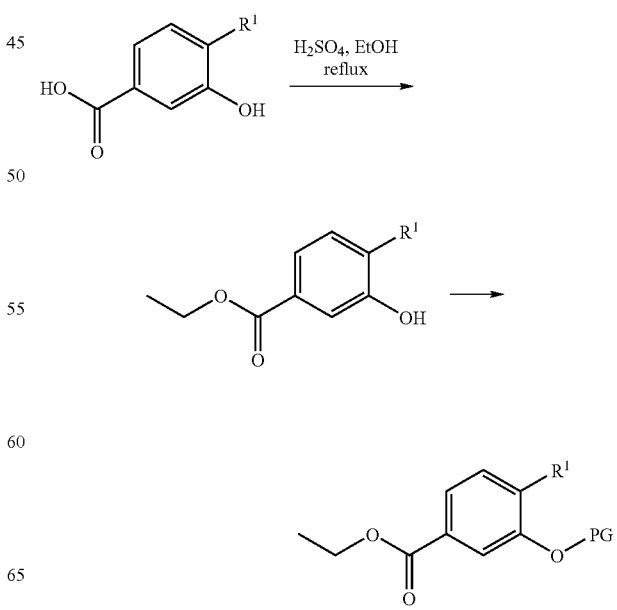

Scheme 1

Scheme 2
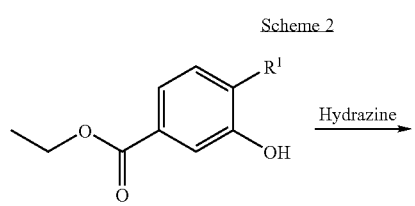
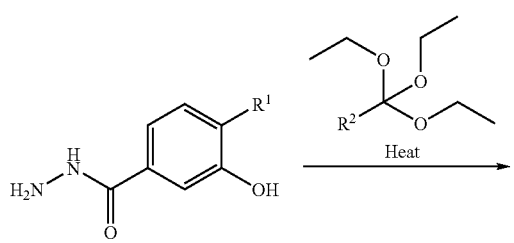
Scheme 3
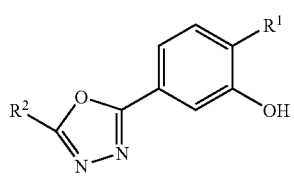
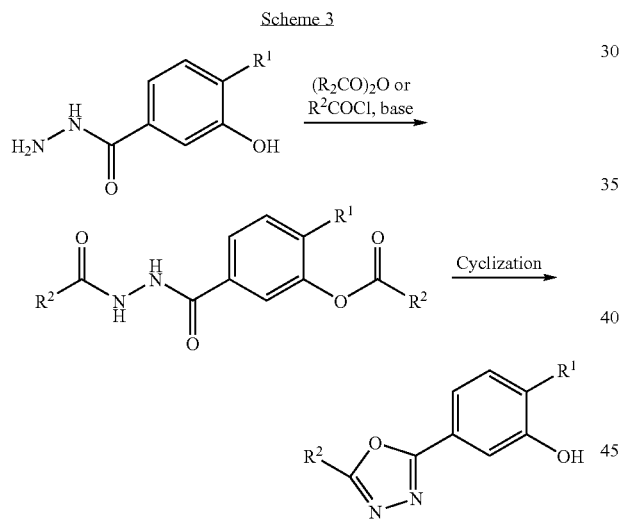
Scheme 4
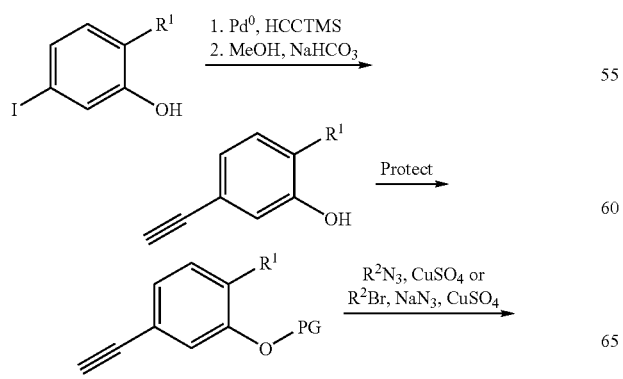
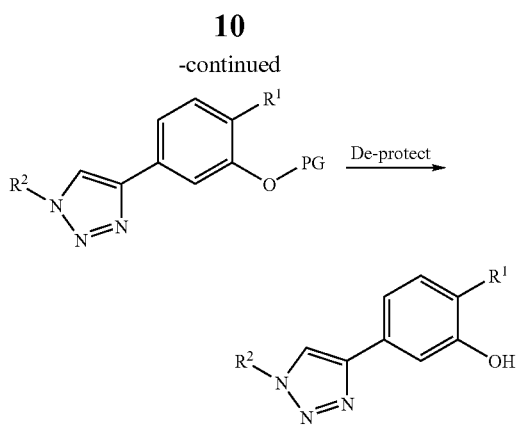
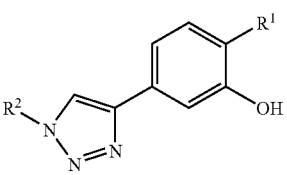
Scheme 5
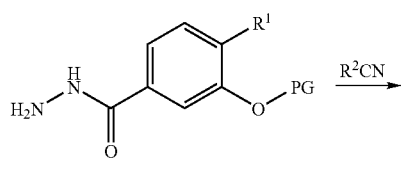
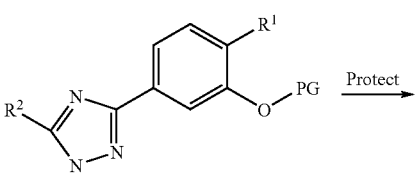
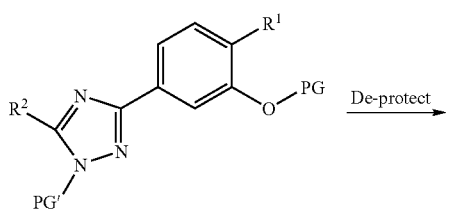
Scheme 6
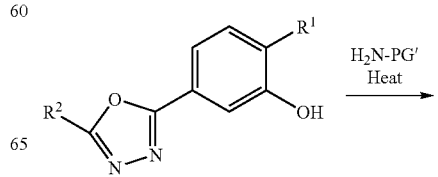

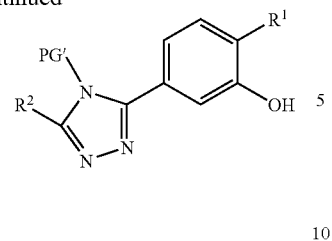

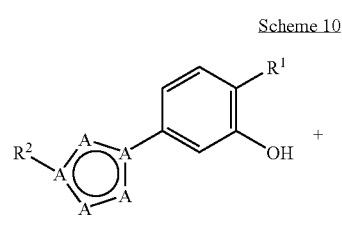

Scheme 10

Scheme 7

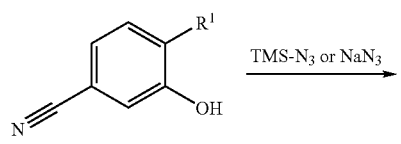

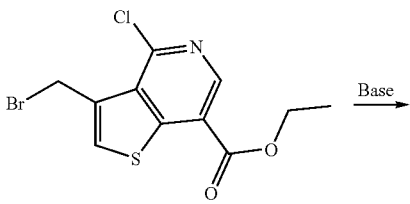

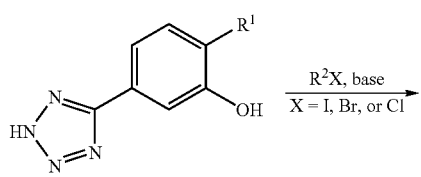

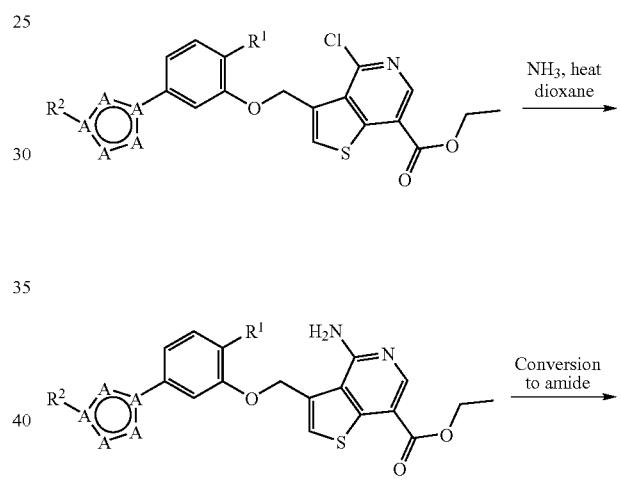

Scheme 8

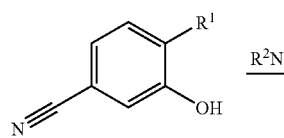

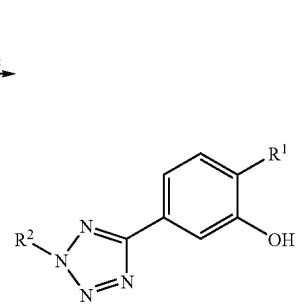

The above schemes are general in nature. $R^1$, $R^2$, and $R^3$ in the above schemes are as defined hereinabove for formula I. The reaction conditions, materials used, and amounts of materials used will depend upon the product to be formed. PG and PG' refer generally to protecting groups and R and R' refer generally to substituent groups. These will also depend upon the materials used and the product to be formed. The following examples illustrate specific reaction conditions, materials, amounts of materials, and protecting groups which may be used in the practice of the present invention. The examples Scheme 9

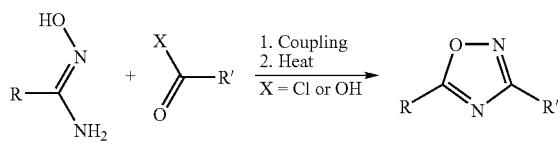

Example 1

3-Bromomethyl-4-chloro-thieno[3,2-c]pyridine-7-carboxylic acid ethyl ester

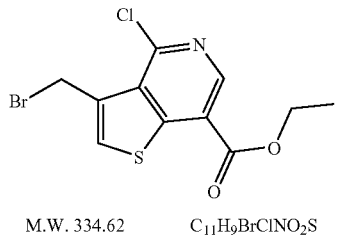

M.W. 334.62    C₁₁H₉BrClNO₂S

The 3-bromomethyl-4-chloro-thieno[3,2-c]pyridine-7-carboxylic acid ethyl ester starting material was prepared from 3-methylthiophene according to the procedure of Luk, K.; McDermott, L. A.; Rossman, P. L.; Wovkulich, P. M.; Zhang, Z. US Patent 20050256154 A1.

Example 2

3-Hydroxy-4-methyl-benzoic acid ethyl ester

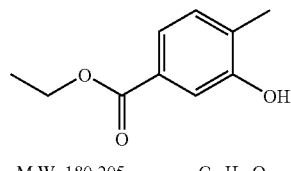

M.W. 180.205    C₁₀H₁₂O₃

A mixture of 3-hydroxy-4-methylbenzoic acid (25.42 g, 167 mmol) (TCI US) and concentrated sulfuric acid (3 mL) in absolute ethanol (180 mL) was heated at reflux for 20 hours. After cooling, solid sodium bicarbonate (10 g) was added to neutralize the acid. Mixture was partitioned between diethyl ether (2×400 mL) and water (2×300 mL). Organic layers were washed with brine (300 mL), combined, dried (MgSO₄), filtered, and concentrated. Residue was recrystallized from hexanes to give 3-hydroxy-4-methyl-benzoic acid ethyl ester as white crystals in two crops. (Yield 29.14 g, 96.8%).

Example 3

3-Methoxymethoxy-4-methyl-benzoic acid ethyl ester

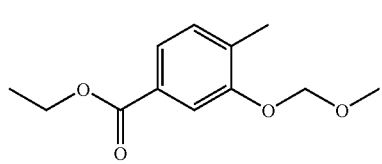

M.W. 224.259    C₁₂H₁₆O₄

N,N-Diisopropylethylamine (5.3 mL, 30.5 mmol) (Aldrich) was added to a suspension of ethyl 3-hydroxy-4-methylbenzoate (5.0 g, 27.75 mmol) (from Example 2 supra) in dichloromethane (20 mL) with cooling in an ice-water bath. Chloromethylmethyl ether (4.2 mL, 55.5 mmol) (Aldrich) was then added dropwise and the mixture stirred at room temperature for 5 hours. The mixture was then diluted with ether (100 mL) and washed with mixture of water (100 mL), followed by 0.1 N HCl (2×100 mL) and brine (100 mL). Aqueous layers were back washed with ether (100 mL). Organic solutions were combined, dried (MgSO₄), filtered and concentrated. Residue was filtered through silica gel (Biotage 40 L) eluting with dichloromethane. Fractions were combined and concentrated to give 3-methoxymethoxy-4-methyl-benzoic acid ethyl ester as colorless oil. (Yield 4.88 g, 78.4%).

Example 4

4-Methyl-3-(2-trimethylsilanyl-ethoxymethoxy)-benzoic acid ethyl ester

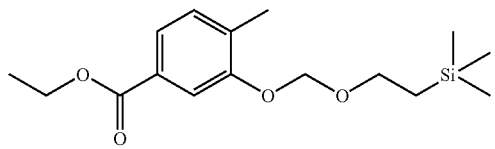

M.W. 310.469    C₁₆H₂₆O₄Si

Sodium hydride (60% in oil, 1.80 g, 45 mmol) (Aldrich) washed with pentane (2×50 mL), pentane was removed by pipetting. Resulting solid was suspended in anhydrous N,N-dimethylformamide (15 mL) and cooled in an ice-water bath. A solution of ethyl 3-hydroxy-4-methylbenzoate (5.41 g, 30 mmol) (from Example 2 supra) in N,N-dimethylformamide (10 mL) was added dropwise over 30 minutes. After stirring for another 30 minutes 2-(trimethylsilyl-ethoxymethyl chloride (6.4 mL, 36 mmol) (Aldrich) was added dropwise over 10 minutes. After stirring at room temperature for another 2 hours, the reaction mixture was partitioned between water (3×100 mL) and diethyl ether (2×100 mL). Organic layers were washed with brine (100 mL), then combined, dried (MgSO₄), filtered and concentrated to give crude 4-methyl-3-(2-trimethylsilanyl-ethoxymethoxy)-benzoic acid ethyl ester as colorless oil. This was used in the next step without further purification. (Yield 9.00 g, 96.6%).

Example 5

2-Methyl-5-[4-methyl-3-(2-trimethylsilanyl-ethoxymethoxy)-phenyl]-[1,3,4]oxadiazole

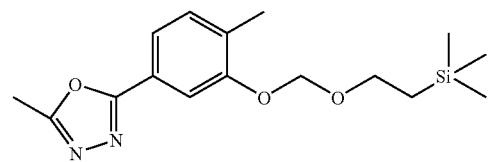

M.W. 320.467    C₁₆H₂₄N₂O₃Si

A suspension of crude 4-methyl-3-(2-trimethylsilanyl-ethoxymethoxy)-benzoic acid ethyl ester (9.0 g, 29 mmol) (from Example 4 supra) in anhydrous hydrazine (10 mL, 318 mmol) (Aldrich) was heated at reflux (150° C. bath temperature) for 1.5 hours. After cooling to room temperature, mixture was partitioned between ethyl acetate (2×100 mL) and water (3×100 mL, with a few mL of brine added). Organic layers were washed with brine (100 mL), then combined, dried (MgSO$_4$), filtered and concentrated. Residue was diluted with ethanol (300 mL) and concentrated to give the intermediate hydrazide as a white solid. This was suspended in triethyl orthoacetate (20 mL, 109 mmol) (Aldrich) and heated at reflux (150° C. bath temperature) for 22 hours. After cooling mixture was diluted with hexanes and purified by flash chromatography (Biotage 40 L, 5%, then 25% ethyl acetate in hexanes as solvent). Fractions were combined and concentrated to give 2-methyl-5-[4-methyl-3-(2-trimethylsilanyl-ethoxymethoxy)-phenyl]-[1,3,4]oxadiazole as a pale yellow oil which crystallized as white crystals on standing. (Yield 8.22 g, 88.5%).

Example 6

3-Hydroxy-4-methyl-benzoic acid hydrazide

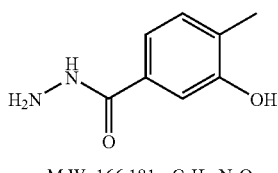

M.W. 166.181  C$_8$H$_{10}$N$_2$O$_2$

A suspension of ethyl 3-hydroxy-4-methylbenzoate (14.42 g, 80 mmol) (from Example 2 supra) in anhydrous hydrazine (30 mL, 956 mmol) (Aldrich) was heated at reflux (150° C. bath temperature) for 2.0 hours. After cooling to room temperature, mixture was concentrated under reduced pressure (high vacuum) to give crude 3-hydroxy-4-methyl-benzoic acid hydrazide as an off-white solid. (Yield 13.26 g, 100%).

Example 7

3-(5-Methyl-[1,3,4]oxadiazol-2-yl)-phenol

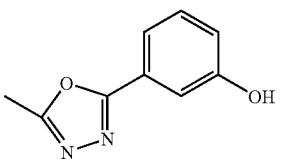

36721-179B  M.W. 176.176  C$_9$H$_8$N$_2$O$_2$

Mixture of 3-hydroxybenzoic hydrazide (0.91 g, 6 mmol) (Aldrich) and triethyl orthoacetate (4.5 mL, 24 mmol) (Aldrich) was heated in a 150° C. bath in a sealed pressure reactor for 22 hours. After cooling to room temperature, mixture was concentrated and residue purified by flash chromatography (Biotage 40 L, ethyl acetate-hexanes 1:1 as solvent) to give 2 products. The higher Rf material was recrystallized from dichloromethane-hexanes to give 2-(3-ethoxy-phenyl)-5-methyl-[1,3,4]oxadiazole as white crystals (Yield 0.29 g, 23.7%). The lower Rf material was recrystallized from dichloromethane-hexanes to give 3-(5-methyl-[1,3,4]oxadiazol-2-yl)-phenol as white crystals. (Yield 0.77 g, 72.8%).

Example 8

4-Chloro-3-[3-(5-methyl-[1,3,4]oxadiazol-2-yl)-phenoxymethyl]-thieno[3,2-c]pyridine-7-carboxylic acid ethyl ester

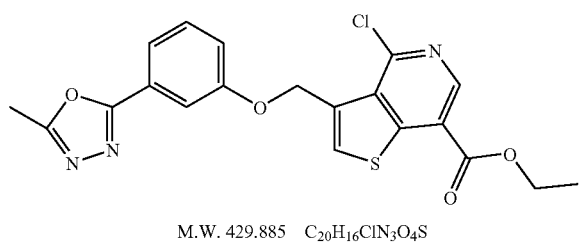

M.W. 429.885  C$_{20}$H$_{16}$ClN$_3$O$_4$S

A suspension of 3-(5-methyl-[1,3,4]oxadiazol-2-yl)-phenol (0.15 g, 0.85 mmol) (from Example 7 supra), potassium carbonate (0.25 g, 1.8 mmol) and 18-Crown-6 (10 mg, 0.04 mmol) (Aldrich) in N,N-dimethylformamide (5 mL) was heated at 65° C. in a sealed tube with magnetic stirring for 2 hours. 3-Bromomethyl-4-chloro-thieno[3,2-c]pyridine-7-carboxylic acid ethyl ester (0.27 g, 0.8 mmol) (from Example 1 supra) and potassium iodide (0.13 g, 0.8 mmol) were then added and mixture heated at 65° C. in the sealed tube for another 20 hours. After cooling, mixture was partitioned between ethyl acetate (2×100 mL) and water (2×100 mL). Organic layers were washed with brine, then combined, dried (MgSO$_4$), filtered and concentrated. Residue was purified by flash chromatography (Biotage 40S, 20% ethyl acetate in dichloromethane as solvent) to give 4-chloro-3-[3-(5-methyl-[1,3,4]oxadiazol-2-yl)-phenoxymethyl]-thieno[3,2-c]pyridine-7-carboxylic acid ethyl ester as a white powder. (Yield 0.22 g, 63.1%).

Example 9

4-Amino-3-[3-(5-methyl-[1,3,4]oxadiazol-2-yl)-phenoxymethyl]-thieno[3,2-c]pyridine-7-carboxylic acid ethyl ester

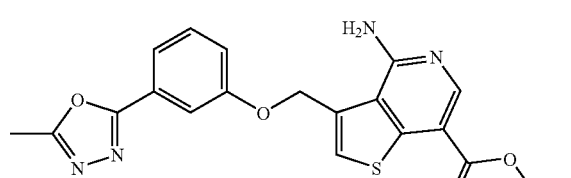

37009-142A  M.W. 410.455  C$_{20}$H$_{18}$N$_4$O$_4$S

Ammonia gas was bubbled into a solution of 4-chloro-3-[3-(5-methyl-[1,3,4]oxadiazol-2-yl)-phenoxymethyl]-thieno[3,2-c]pyridine-7-carboxylic acid ethyl ester (0.12 g, 0.29 mmol) (from Example 8 supra) in 2-propanol (15 mL) for 20 minutes. The mixture was heated in a microwave reactor at 140° C. for 2 hours. The reaction mixture was concentrated.

The residue washed with hot methanol, filtered and dried to give 4-amino-3-[3-(5-methyl-[1,3,4]oxadiazol-2-yl)-phenoxymethyl]-thieno[3,2-c]pyridine-7-carboxylic acid ethyl ester. (Yield 0.07 g, 58%).

HRMS (ES+) m/z Calcd for $C_{20}H_{18}N_4O_4S$+H [(M+H)+]: 411.1122. Found: 411.1121.

Example 10

4-Amino-3-[3-(5-methyl-[1,3,4]oxadiazol-2-yl)-phenoxymethyl]-thieno[3,2-c]pyridine-7-carboxylic acid (2-hydroxy-ethyl)-amide

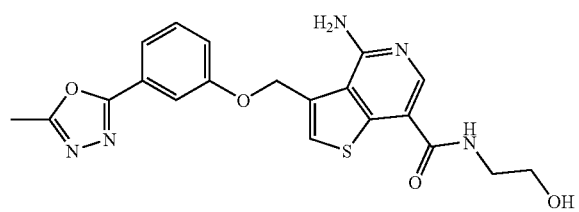

37009-143A   M.W. 425.470   $C_{20}H_{19}N_5O_4S$

A solution of 4-amino-3-[3-(5-methyl-[1,3,4]oxadiazol-2-yl)-phenoxymethyl]-thieno[3,2-c]pyridine-7-carboxylic acid ethyl ester (0.05 g, 0.12 mmol) (from Example 9 supra) in dimethylsulfoxide (0.5 mL) was treated with ethanolamine (1.5 mL) (Aldrich) and heated at 160° C. for 2 hours in a microwave reactor. The reaction mixture was purified by reverse-phase chromatography (C18 column) eluting with acetonitrile-water to give 4-amino-3-[3-(5-methyl-[1,3,4]oxadiazol-2-yl)-phenoxymethyl]-thieno[3,2-c]pyridine-7-carboxylic acid (2-hydroxy-ethyl)-amide as a white powder. (Yield 15.0 mg, 29%).

HRMS (ES+) m/z Calcd for $C_{20}H_{19}N_5O_4S$+H [(M+H)+]: 426.1231. Found: 426.1227.

Example 11

2-Methyl-5-(5-methyl-[1,3,4]oxadiazol-2-yl)-phenol

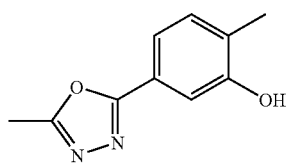

M.W. 190.203   $C_{10}H_{10}N_2O_2$

A suspension of ethyl 3-hydroxy-4-methylbenzoate (3.60 g, 20 mmol) (from Example 6 supra) in anhydrous hydrazine (10 mL, 318 mmol) (Aldrich) was heated at reflux (150° C. bath temperature) for 3 hours. After cooling to room temperature, mixture was concentrated under reduced pressure to give a dry solid. This was suspended in xylene (50 mL) and concentrated under reduced pressure. Resulting solid was suspended in triethyl ortho-aceate (35 mL, 191 mmol) (Aldrich) and heated at reflux (150° C. bath temperature) for 20 hours with removal of ethanol. After cooling, dichloromethane was added and solid was collected by filtration to give 2-methyl-5-(5-methyl-[1,3,4]oxadiazol-2-yl)-phenol as an off-white crystalline material. (Yield 2.28 g, 60.0%).

Filtrate from above was purified by flash chromatography (Biotage 40 L, 10% then 40% ethyl acetate in dichloromethane as solvent) to give second crop of 2-methyl-5-(5-methyl-[1,3,4]oxadiazol-2-yl)-phenol as a white crystalline material. (Yield 0.99 g, 26.0%).

Example 12

4-Chloro-3-[2-methyl-5-(5-methyl-[1,3,4]oxadiazol-2-yl)-phenoxymethyl]-thieno[3,2-c]pyridine-7-carboxylic acid ethyl ester

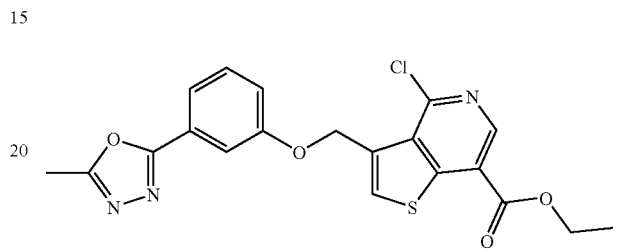

M.W. 443.912   $C_{21}H_{18}ClN_3O_4S$

A suspension of 3-bromomethyl-4-chloro-thieno[3,2-c]pyridine-7-carboxylic acid ethyl ester (0.29 g, 0.87 mmol) (from Example 1 supra), potassium iodide (0.14 g, 0.87 mmol), 2-methyl-5-(5-methyl-[1,3,4]oxadiazol-2-yl)-phenol (0.17 g, 0.9 mmol) (from Example 11 supra), potassium carbonate (0.27 g, 1.9 mmol) and 18-Crown-6 (10 mg, 0.04 mmol) (Aldrich) in N,N-dimethylformamide (5 mL) was heated at 65° C. in a sealed tube with magnetic stirring for 20 hours. After cooling, mixture was partitioned between ethyl acetate (2×100 mL) and water (2×100 mL). Aqueous layers were extracted with dichloromethane (2×100 mL). [Material was more soluble in dichloromethane than ethyl acetate.] Organic layers were washed with brine, then combined, dried (MgSO4), filtered and concentrated. Residue was purified by flash chromatography (Biotage 40S, dichloromethane then 20% ethyl acetate in dichloromethane as solvent) to give 4-chloro-3-[2-methyl-5-(5-methyl-[1,3,4]oxadiazol-2-yl)-phenoxymethyl]-thieno[3,2-c]pyridine-7-carboxylic acid ethyl ester as a white powder. (Yield 0.24 g, 62.4%).

Example 13

4-Amino-3-[2-methyl-5-(5-methyl-[1,3,4]oxadiazol-2-yl)-phenoxymethyl]-thieno[3,2-c]pyridine-7-carboxylic acid ethyl ester

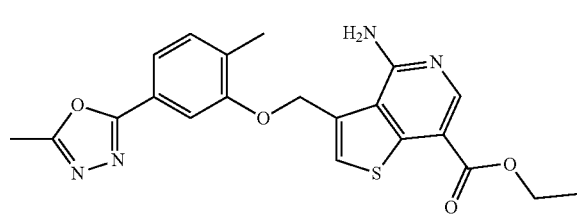

37009-145A   M.W. 424.482   $C_{21}H_{20}N_4O_4S$

Ammonia gas was bubbled into a solution of 4-chloro-3-[2-methyl-5-(5-methyl-[1,3,4]oxadiazol-2-yl)-phenoxy-methyl]-thieno[3,2-c]pyridine-7-carboxylic acid ethyl ester (0.12 g, 0.28 mmol) (from Example 12 supra) in 2-propanol (15 mL) for 20 minutes. The mixture was heated in a microwave reactor at 140° C. for 2 hours. The reaction mixture was concentrated. The residue was purified by flash chromatography eluting with 30% ethyl acetate in dichloromethane to give recovered staring material (25 mg) and 4-amino-3-[2-methyl-5-(5-methyl-[1,3,4]oxadiazol-2-yl)-phenoxymethyl]-thieno[3,2-c]pyridine-7-carboxylic acid ethyl ester as a white powder. (Yield 0.053 g, 44%). HRMS (ES$^+$) m/z Calcd for $C_{21}H_{20}N_4O_4S+H$ [(M+H)$^+$]: 425.1278. Found: 425.1274.

Example 14
4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide trifluoro-acetic acid salt

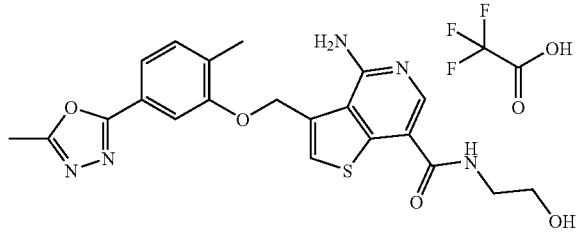

37009-148A    M.W. 439.497 + 114.024    $C_{21}H_{21}N_5O_4S·C_2HF_3O_2$

A solution of 4-amino-3-[2-methyl-5-(5-methyl-[1,3,4]oxadiazol-2-yl)-phenoxymethyl]-thieno[3,2-c]pyridine-7-carboxylic acid ethyl ester (0.043 g, 0.10 mmol) (from Example 13 supra) in dimethylsulfoxide (0.5 mL) was treated with ethanolamine (1.5 mL) (Aldrich) and heated at 160° C. for 2 hours in a microwave reactor. The reaction mixture was purified by HPLC eluting with acetonitrile-water containing trifluoro-acetic acid to give two products. The first product gave 4-amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide trifluoro-acetic acid salt as a white powder. (Yield 20.0 mg, 47%).

HRMS (ES$^+$) m/z Calcd for $C_{21}H_{21}N_5O_4S+H$ [(M+H)$^+$]: 440.1387. Found: 440.1384.

Example 15

4-Amino-3-{5-[4-(2-hydroxy-ethyl)-5-methyl-4H-[1,2,4]triazol-3-yl]-2-methyl-phenoxymethyl}-thieno[3,2-c]pyridine-7-carboxylic acid (2-hydroxy-ethyl)-amide trifluoro-acetic acid salt

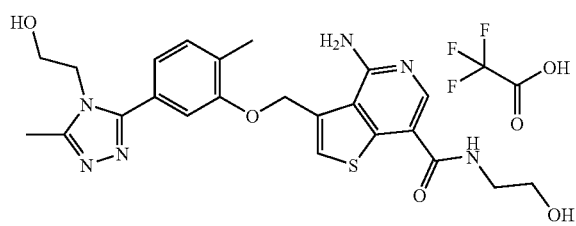

37009-148B    M.W. 482.565 + 114.024    $C_{23}H_{23}N_6O_4S·C_2HF_3O_2$

The second product (from Example 14 supra) gave 4-amino-3-{5-[4-(2-hydroxy-ethyl)-5-methyl-4H-[1,2,4]triazol-3-yl]-2-methyl-phenoxy-methyl}-thieno[3,2-c]pyridine-7-carboxylic acid (2-hydroxy-ethyl)-amide trifluoroacetic acid salt. (Yield 10.0 mg, 21%).

HRMS (ES$^+$) m/z Calcd for $C_{23}H_{26}N_6O_4S+H$ [(M+H)$^+$]: 483.1809. Found: 483.1808.

Example 16

4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide toluene-4-sulfonic acid salt

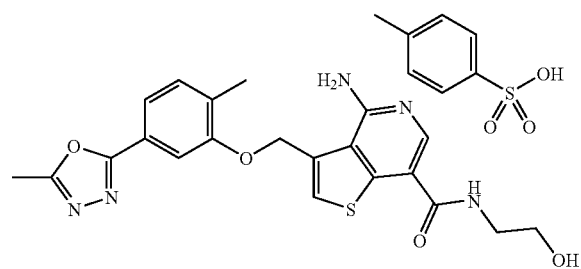

37009-187A    M.W. 439.497 + 172.204    $C_{21}H_{21}N_5O_4S·C_7H_8O_3S$

To a solution of 4-amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide (0.045 g, 0.10 mmol) (from Example 14 supra) in methanol (6 mL) was treated with toluene-4-sulfonic acid hydrate (19.5 mg, 0.10 mmol) (Aldrich) and heated at 40° C. for 30 minutes. The solution was concentrated. The residue washed with diethyl ether, dissolved ino water and lyophilized to give 4-amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide toluene-4-sulfonic acid salt. (Yield 60.8 mg, 97%).

HRMS (ES$^+$) m/z Calcd for $C_{21}H_{21}N_5O_4S+H$ [(M+H)$^+$]: 440.1387. Found: 440.1384.

Example 17

5-Iodo-2-methyl-phenol

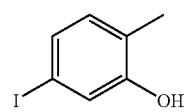

M.W. 234.038    $C_7H_7IO$

5-Iodo-2-methyl-phenol was prepared according to the procedure of Laugraud, S.; Reinier, N. WO96/32399, Published Oct. 17, 1996.

A solution of 5-amino-O-cresol (10.0 g, 81 mmol) (Aldrich) in a mixture of tetrahydrofuran (100 mL), water (150 mL) and concentrated sulfuric acid (6 mL, 0.11 mmol) was cooled in an ice-water bath. A solution of sodium nitrite (5.6 g, 81 mmol) in water (30 mL) was added dropwise over 30 minutes. Mixture was stirred with cooling for another 30 minutes. (A suspension formed). Powder copper metal (200 mg, 3 mmol) was added followed by a solution of potassium iodide (17.5 g, 0.11 mmol) in water (70 mL). Mixture was allowed to warm to room temperature and stirred for 90 minutes then poured into water (200 mL). Mixture was extracted with ethyl acetate (2×400 mL). Organic layers were washed with water (400 mL) and brine (400 mL), then combined, dried (MgSO$_4$), filtered and concentrated. Residue was purified by flash chromatography (Biotage 75 L, hexanes-dichloromethane 2:3 as solvent). Pure fractions were combined and material recrystallized from hexanes to give 5-iodo-2-methyl-phenol as white needles in 2 crops. (Yield 10.08 g, 53.0%).

Example 18

4-Iodo-2-methoxymethoxy-1-methyl-benzene

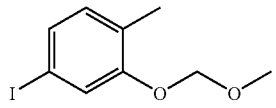

M.W. 278.091  C$_9$H$_{11}$IO$_2$

N,N-Diisopropylethylamine (8.3 mL, 47.4 mmol) (Aldrich) was added to a suspension of 5-iodo-2-methyl-phenol (10.1 g, 43.1 mmol) (from Example 17 supra) in dichloromethane (40 mL) with cooling in an ice-water bath. Chloromethyl-methyl ether (6.5 mL, 86.1 mmol) (Aldrich) was added dropwise and the mixture stirred at room temperature for 5 hours. The mixture was then diluted with ether (200 mL) and washed with water (200 mL), followed by 0.1 N HCl (2×200 mL) and brine (200 mL). Aqueous layers were back washed with ether (200 mL). Organic solutions were combined, dried (MgSO$_4$), filtered and concentrated. Residue was filtered through silica gel (Biotage 40 L) eluting with dichloromethane-hexenaes (1:4 V/v). Fractions were combined and concentrated to give 4-iodo-2-methoxymethoxy-1-methyl-benzene as colorless oil. (Yield 9.05 g, 75.6%).

Example 19

4-Ethynyl-2-methoxymethoxy-1-methyl-benzene

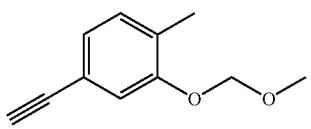

M.W. 176.217  C$_{11}$H$_{12}$O$_2$

Argon was bubbled into a mixture of the 4-iodo-2-methoxymethoxy-1-methyl-benzene (7.63 g, 27.5 mmol) (from example 18 supra), triethylamine (55 mL) (Aldrich) and acetonitrile (100 mL) in a pressure reactor for 20 minutes at room temperature. Ethynyltrimethylsilane (9.2 mL, 64.5 mmol) (Aldrich), copper(I) iodide (245 mg, 1.28 mmol) (Aldrich) and dichlorobis(triphenylphosphine)palladium(II) (911 mg, 1.29 mmol) (Aldrich) were added. Reactor was capped and mixture heated at 100° C. for 5 hours with magnetic stirring. After cooling to room temperature, mixture was suspended in diethyl ether (250 mL) and water (250 mL) and filtered through Celite®. Layers were separated. Organic layer washed with water (250 mL) and brine (250 mL). Aqueous layers were back washed with ether (250 mL). Organic layers were combined, dried (MgSO$_4$), filtered and concentrated. Residue was dissolved in methanol (50 mL) and potassium carbonate (500 mg) was added. Mixture was stirred at room temperature overnight. After concentrating, residue was partitioned between diethyl ether (2×250 mL) and water (2×250 mL). Organic layers were washed with brine (200 mL), combined, dried (MgSO$_4$), filtered and concentrated. Residue was purified by flash chromatography (Biotage 40 L, hexanes, then hexanes-dichloromethane 9:1 and 3:1 as solvent) to give 4-ethynyl-2-methoxymethoxy-1-methyl-benzene as a brown oil. (Yield 4.65 g, 96.2%).

Example 20

4-(3-Methoxymethoxy-4-methyl-phenyl)-1-methyl-1H-[1,2,3]triazole

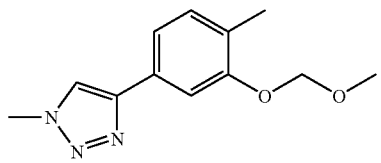

M.W. 233.27  C$_{12}$H$_{15}$N$_3$O$_2$

To a suspension of 4-ethynyl-2-methoxymethoxy-1-methyl-benzene (0.64 g, 3.63 mmol) (from Example 19 supra), iodomethane (0.23 mL, 3.63 mmol) (Aldrich) and sodium azide (0.24 g, 3.63 mmol) (Aldrich) in a mixture of water (6 mL) and t-butanol (6 mL) was added copper powder (0.17 g, 2.68 mmol) and aqueous copper sulphate solution (1 N, 0.7 mL). The reaction mixture was heated at 125° C. for 20 minutes in a microwave reactor. After cooling, the reaction mixture was partitioned between ethyl acetate and water. The aqueous phase was extracted with ethyl acetate (2×). The combined organic phase was washed with water and brine, dried (MgSO$_4$) and concentrated. The residue was purified by flash chromatography eluting with 5-60% ethyl acetate in hexanes to give 4-(3-methoxymethoxy-4-methyl-phenyl)-1-methyl-1H-[1,2,3]triazol. (Yield 0.57 g, 67%).

Example 21

2-Methyl-5-(1-methyl-1H-[1,2,3]triazol-4-yl)-phenol

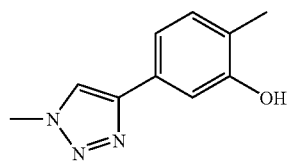

M.W. 189.219  C$_{10}$H$_{11}$N$_3$O

To a solution of 4-(3-methoxymethoxy-4-methyl-phenyl)-1-methyl-1H-[1,2,3]triazol (0.57 g, 2.44 mmol) (from Example 20 supra) in tetrahydrofuran-2-propanol (1:1, 20 mL) was added HCl in dioxane (4 M, 8 mL) (Aldrich). The reaction mixture was stirred at room temperature for 2 days.

The solution was concentrated. The residue was diluted with ethyl acetate, washed with saturated aqueous sodium bicarbonate solution and brine, dried (MgSO$_4$) and concentrated. The residue was recrystallized from ethyl acetate-hexanes and dried to give 2-methyl-5-(1-methyl-1H-[1,2,3]triazol-4-yl)-phenol. (Yield 0.24 g, 52%).

Example 22

4-Chloro-3-[2-methyl-5-(1-methyl-1H-[1,2,3]triazol-4-yl)-phenoxymethyl]-thieno[3,2-c]pyridine-7-carboxylic acid ethyl ester

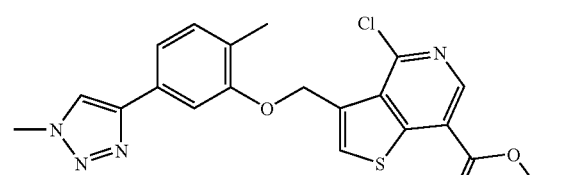

M.W. 442.928   C$_{21}$H$_{19}$ClN$_4$O$_4$S

A suspension of cesium carbonate (0.56 g, 1.73 mmol) (Aldrich), 2-methyl-5-(1-methyl-1H-[1,2,3]triazol-4-yl)-phenol (0.24 g, 1.27 mmol) (from Example 21 supra) in tetrahydrofuran-N,N-dimethylformamide (5:2, 17.5 mL) was heated at 70° C. for 3 hours. 3-Bromomethyl-4-chloro-thieno[3,2-c]pyridine-7-carboxylic acid ethyl ester (0.40 g, 1.15 mmol) (from Example 1 supra) was added. Heating was continued for 18 hours. The reaction mixture was partitioned between ethyl acetate and water. The aqueous phase was extracted with ethyl acetate (2×). The combined organic phase washed with water and brine, dried (MgSO$_4$) and concentrated. The residue was purified by flash chromatography eluting with 30% ethyl acetate in dichloromethane to give 4-chloro-3-[2-methyl-5-(1-methyl-1H-[1,2,3]triazol-4-yl)-phenoxy-methyl]-thieno[3,2-c]pyridine-7-carboxylic acid ethyl ester. (Yield 0.25 g, 48%).

Example 23

4-Amino-3-[2-methyl-5-(1-methyl-1H-[1,2,3]triazol-4-yl)-phenoxymethyl]-thieno[3,2-c]pyridine-7-carboxylic acid ethyl ester

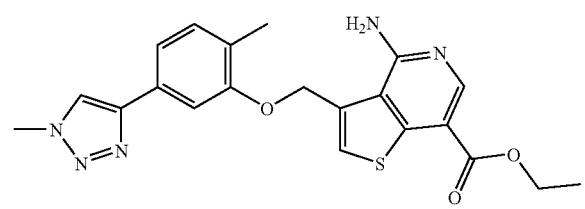

37009-158A   M.W. 423.497   C$_{21}$H$_{21}$N$_5$O$_4$S

Ammonia gas was bubbled into a solution of 4-chloro-3-[2-methyl-5-(1-methyl-1H-[1,2,3]triazol-4-yl)-phenoxymethyl]-thieno[3,2-c]pyridine-7-carboxylic acid ethyl ester (0.17 g, 0.38 mmol) (from Example 22 supra) in 2-propanol (15 mL) for 20 minutes. The mixture was heated in a microwave reactor at 140° C. for 2 hours. The reaction mixture was concentrated. The residue washed with hot methanol, filtered and dried to give 4-amino-3-[2-methyl-5-(1-methyl-1H-[1,2,3]triazol-4-yl)-phenoxymethyl]-thieno[3,2-c]pyridine-7-carboxylic acid ethyl ester as a white powder. (Yield 0.10 g, 63%).

HRMS (ES$^+$) m/z Calcd for C$_{21}$H$_{21}$N$_5$O$_3$S+H [(M+H)$^+$]: 424.1438. Found: 424.1436.

Example 24

4-Amino-3-[2-methyl-5-(1-methyl-1H-[1,2,3]triazol-4-yl)-phenoxymethyl]-thieno[3,2-c]pyridine-7-carboxylic acid (2-hydroxy-ethyl)-amide

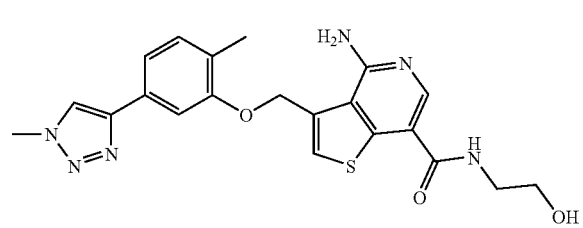

37009-159A   M.W. 438.512   C$_{12}$H$_{22}$N$_6$O$_3$S

A solution of 4-amino-3-[2-methyl-5-(1-methyl-1H-[1,2,3]triazol-4-yl)-phenoxymethyl]-thieno[3,2-c]pyridine-7-carboxylic acid ethyl ester (0.050 g, 0.11 mmol) (from Example 23 supra) in dimethylsulfoxide (0.5 mL) was treated with ethanolamine (1.5 mL) (Aldrich) and heated at 160° C. for 2 hours in a microwave reactor. The reaction mixture was purified by C18 column eluting with acetonitrile-water to give 4-amino-3-[2-methyl-5-(1-methyl-1H-[1,2,3]triazol-4-yl)-phenoxymethyl]-thieno[3,2-c]pyridine-7-carboxylic acid (2-hydroxy-ethyl)-amide as a white powder. (Yield 31.0 mg, 60%).

HRMS (ES$^+$) m/z Calcd for C$_{21}$H$_{22}$N$_6$O$_3$S+H [(M+H)$^+$]: 439.1547. Found: 439.1545.

Example 25

3-(2H-Tetrazol-5-yl)-phenol

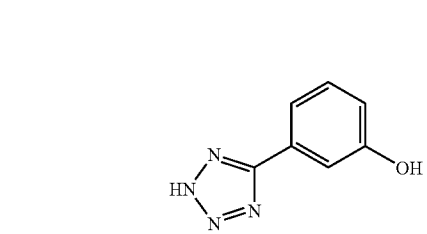

M.W. 162.15   C$_7$H$_6$N$_4$O

A mixture of 3-cyanophenol (4.14 g, 34.75 mmol) (Aldrich), sodium azide (2.49 g, 38.23 mmol) (Aldrich) and ammonium chloride (2.05 g, 38.23 mmol) in N,N-dimethylformamide (30 mL) were heated to 160° C. for 18 hours. The reaction mixture was concentrated. The residue was purified by C18 column eluting with acetonitrile-water to give 3-(2H-tetrazol-5-yl)-phenol. (Yield 0.9 g, 16%).

Example 26

3-[2-(4-Methoxy-benzyl)-2H-tetrazol-5-yl]-phenol

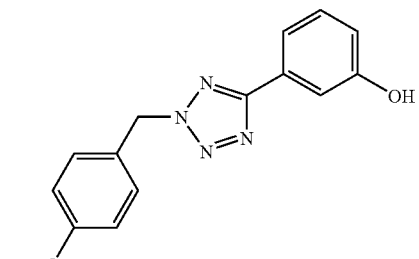

M.W. 282.304  $C_{15}H_{14}N_4O_2$

A suspension of 4-methoxybenzylchloride (0.26 mL, 1.94 mmol) (Aldrich), potassium iodide (0.31 g, 1.85 mmol) (Aldrich), 3-(2H-tetrazol-5-yl)-phenol (0.3 g, 1.85 mmol) (from Example 25 supra), potassium carbonate (0.38 g, 2.78 mmol) and 18-crown-6 (24.0 mg, 0.09 mmol) (Aldrich) in N,N-dimethylformamide (15 mL) was heated at 65° C. for 1 day. The reaction mixture was partitioned between ethyl acetate and water. The aqueous phase was extracted with ethyl acetate (2×). The combined organic phase washed with water and brine, dried ($MgSO_4$) and concentrated. The residue was purified by flash chromatography eluting with 5-40% ethyl acetate in hexanes to give 3-[2-(4-methoxy-benzyl)-2H-tetrazol-5-yl]-phenol. (Yield 0.38 g, 73%).

Example 27

4-Chloro-3-{3-[2-(4-methoxy-benzyl)-2H-tetrazol-5-yl]-phenoxymethyl}-thieno[3,2-c]pyridine-7-carboxylic acid ethyl ester

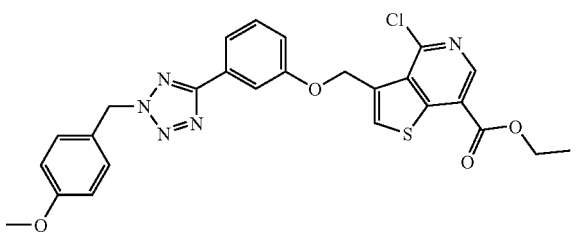

M.W. 536.013  $C_{26}H_{22}ClN_5O_4S$

A suspension of cesium carbonate (0.60 g, 1.83 mmol), 3-[2-(4-methoxy-benzyl)-2H-tetrazol-5-yl]-phenol (0.38 g, 1.35 mmol) (from Example 26 supra) in tetrahydrofuran-N,N-dimethylformamide (5:2, 17.5 mL) was heated at 70° C. for 3 hours. 3-Bromomethyl-4-chloro-thieno[3,2-c]pyridine-7-carboxylic acid ethyl ester (0.41 g, 1.22 mmol) (from Example 1 supra) was added. Heating was continued for 18 hours. The reaction mixture was partitioned between ethyl acetate and water. The aqueous phase was extracted with ethyl acetate (2×). The combined organic phase washed with water and brine, dried ($MgSO_4$) and concentrated. The residue was purified by flash chromatography eluting with 30% ethyl acetate in hexanes to give 4-chloro-3-{3-[2-(4-methoxy-benzyl)-2H-tetrazol-5-yl]-phenoxymethyl}-thieno[3,2-c]pyridine-7-carboxylic acid ethyl ester. (Yield 0.17 g, 26%).

Example 28

4-Amino-3-{3-[2-(4-methoxy-benzyl)-2H-tetrazol-5-yl]-phenoxymethyl}-thieno[3,2-c]pyridine-7-carboxylic acid ethyl ester

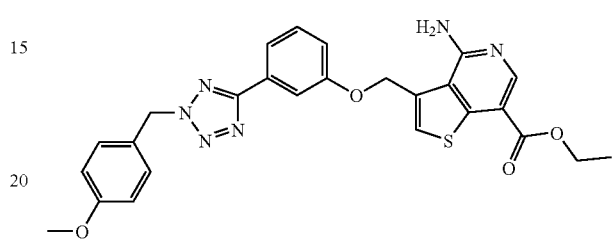

37009-202A  M.W. 516.583  $C_{26}H_{24}N_6O_4S$

Ammonia gas was bubbled into a solution of 4-chloro-3-{3-[2-(4-methoxy-benzyl)-2H-tetrazol-5-yl]-phenoxy-methyl}-thieno[3,2-c]pyridine-7-carboxylic acid ethyl ester (0.17 g, 0.32 mmol) (from Example 27 supra) in 2-propanol (15 mL) for 20 minutes. The mixture was heated in a microwave reactor at 140° C. for 2 hours. The reaction mixture was concentrated. The residue washed with hot methanol, filtered and dried to give 4-amino-3-{3-[2-(4-methoxy-benzyl)-2H-tetrazol-5-yl]-phenoxymethyl}-thieno[3,2-c]pyridine-7-carboxylic acid ethyl ester. (Yield 0.15 g, 94%).

HRMS ($ES^+$) m/z Calcd for $C_{26}H_{24}N_6O_4S+H$ [$(M+H)^+$]: 517.1653. Found: 517.1653.

Example 29

4-Amino-3-{3-[2-(4-methoxy-benzyl)-2H-tetrazol-5-yl]-phenoxymethyl}-thieno[3,2-c]pyridine-7-carboxylic acid (2-hydroxy-ethyl)-amide

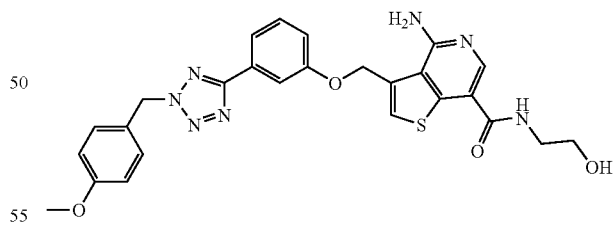

37009-208A  M.W. 531.598  $C_{26}H_{25}N_7O_4S$

A solution of 4-amino-3-{3-[2-(4-methoxy-benzyl)-2H-tetrazol-5-yl]-phenoxymethyl}-thieno[3,2-c]pyridine-7-carboxylic acid ethyl ester (0.050 g, 0.10 mmol) (from Example 28 supra) in dimethylsulfoxide (0.5 mL) was treated with ethanolamine (1.5 mL) (Aldrich) and heated at 160° C. for 2 hours in a microwave reactor. The precipitate was filtered and dried to give 4-amino-3-{3-[2-(4-methoxy-benzyl)-2H-tetrazol-5-yl]-phenoxymethyl}-thieno[3,2-c]pyridine-7-carboxylic acid (2-hydroxy-ethyl)-amide. (Yield 18.0 mg, 35%).

HRMS (ES⁺) m/z Calcd for $C_{26}H_{25}N_7O_4S+H$ [(M+H)⁺]: 532.1762. Found: 532.1762.

Example 30

3-(2-Methyl-2H-tetrazol-5-yl)-phenol

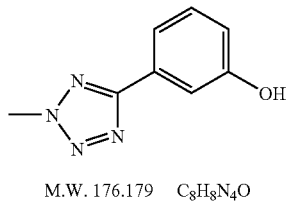

M.W. 176.179   $C_8H_8N_4O$

A suspension of cesium carbonate (0.60 g, 1.83 mmol), 3-(2H-tetrazol-5-yl)-phenol (0.30 g, 1.85 mmol) (from Example 25 supra) in tetrahydrofuran-N,N-dimethylformamide (5:2, 17.5 mL) was heated at 70° C. for 3 hours. Iodomethane (0.29 g, 2.04 mmol) (Aldrich) was added. Heating was continued for 18 hours. The reaction mixture was partitioned between ethyl acetate and water. The aqueous phase was extracted with ethyl acetate (2×). The combined organic phase washed with water and brine, dried (MgSO₄) and concentrated. The residue was purified by flash chromatography eluting with 40% ethyl acetate in hexanes to give 3-(2-methyl-2H-tetrazol-5-yl)-phenol. (Yield 0.23 g, 70%).

Example 31

4-Chloro-3-[3-(2-methyl-2H-tetrazol-5-yl)-phenoxymethyl]-thieno[3,2-c]pyridine-7-carboxylic acid ethyl ester

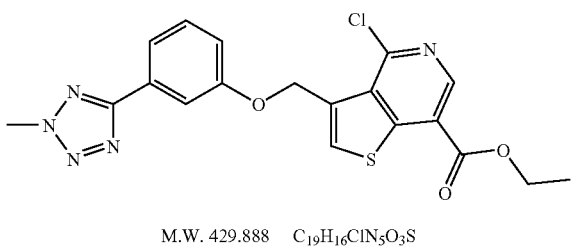

M.W. 429.888   $C_{19}H_{16}ClN_5O_3S$

A mixture of 3-bromomethyl-4-chloro-thieno[3,2-c]pyridine-7-carboxylic acid ethyl ester (042 g, 1.24 mmol) (from Example 1 supra), 3-(2-methyl-2H-tetrazol-5-yl)-phenol (0.23 g, 1.31 mmol) (from Example 30 supra), potassium iodide (0.21 g, 1.24 mmol), potassium carbonate (0.38 g, 2.78 mmol) and 18-crown-6 (16.0 mg, 0.06 mmol) in N,N-dimethylformamide (15 mL) was heated at 65° C. for 1 day. The reaction mixture was partitioned between ethyl acetate and water. The aqueous phase was extracted with ethyl acetate (2×). The combined organic phase washed with water and brine, dried (MgSO₄) and concentrated. The residue was purified by flash chromatography eluting with 30% ethyl acetate in hexanes to give 4-chloro-3-[3-(2-methyl-2H-tetrazol-5-yl)-phenoxymethyl]-thieno[3,2-c]pyridine-7-carboxylic acid ethyl ester. (Yield 0.15 g, 28%).

Example 32

4-Amino-3-[3-(2-methyl-2H-tetrazol-5-yl)-phenoxymethyl]-thieno[3,2-c]pyridine-7-carboxylic acid ethyl ester

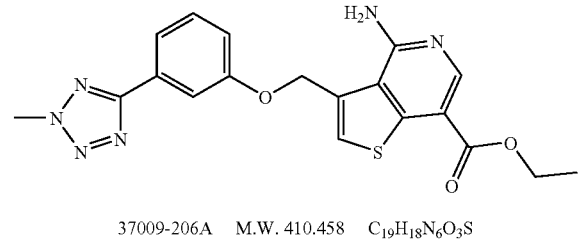

37009-206A   M.W. 410.458   $C_{19}H_{18}N_6O_3S$

Ammonia gas was bubbled into a solution of 4-chloro-3-[3-(2-methyl-2H-tetrazol-5-yl)-phenoxymethyl]-thieno[3,2-c]pyridine-7-carboxylic acid ethyl ester (0.15 g, 0.35 mmol) (from Example 31 supra) in 2-propanol (15 mL) for 20 minutes. The mixture was heated in a microwave reactor at 140° C. for 2 hours. The reaction mixture was concentrated. The residue washed with hot methanol, filtered and dried to give 4-amino-3-[3-(2-methyl-2H-tetrazol-5-yl)-phenoxymethyl]-thieno[3,2-c]pyridine-7-carboxylic acid ethyl ester as a white powder. (Yield 0.11 g, 79%).

HRMS (ES⁺) m/z Calcd for $C_{19}H_{18}N_6O_3S+H$ [(M+H)⁺]: 411.1234. Found: 411.1235.

Example 33

4-Amino-3-[3-(2-methyl-2H-tetrazol-5-yl)-phenoxymethyl]-thieno[3,2-c]pyridine-7-carboxylic acid (2-hydroxy-ethyl)-amide

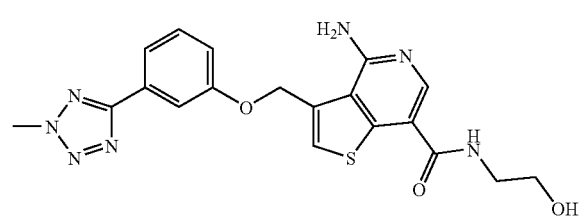

37009-209A   M.W. 425.472   $C_{19}H_{19}N_7O_3S$

A solution of 4-amino-3-[3-(2-methyl-2H-tetrazol-5-yl)-phenoxymethyl]-thieno[3,2-c]pyridine-7-carboxylic acid ethyl ester (0.050 g, 0.12 mmol) (from Example 32 supra) in dimethylsulfoxide (0.5 mL) was treated with ethanolamine (1.5 mL) (Aldrich) and heated at 160° C. for 2 hours in a microwave reactor. The precipitate was filtered, washed with methanol and dried to give 4-amino-3-[3-(2-methyl-2H-tetrazol-5-yl)-phenoxymethyl]-thieno[3,2-c]pyridine-7-carboxylic acid (2-hydroxy-ethyl)-amide as a white powder. (Yield 39.0 mg, 75%).

HRMS (ES⁺) m/z Calcd for $C_{19}H_{19}N_7O_3S+H$ [(M+H)⁺]: 426.1343. Found: 426.1344.

Example 34

5-[1-(4-Chloro-benzyl)-1H-[1,2,3]triazol-4-yl]-2-methyl-phenol

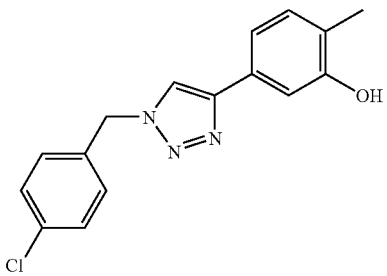

M.W. 299.762  $C_{16}H_{14}ClN_3O$

To a suspension of 4-ethynyl-2-methoxymethoxy-1-methyl-benzene (1.50 g, 8.50 mmol) (from Example 19 supra), 4-chlorobenzyl bromide (1.76 g, 8.50 mmol) and sodium azide (0.56 g, 8.50 mmol) in a mixture of water (12 mL) and t-butanol (12 mL) was added copper powder (0.40 g, 6.30 mmol) and aqueous solution of copper sulphate solution (1 N, 1.64 mL). The reaction mixture was heated at 130° C. for 30 minutes in a microwave reactor. After cooling, the reaction mixture was partitioned between dichloromethane and water. The aqueous phase was extracted with dichloromethane (2×). The combined organic phase washed with water and brine, dried (MgSO₄) and concentrated. The residue was purified by flash chromatography eluting with 40% ethyl acetate in hexanes to give 5-[1-(4-chloro-benzyl)-1H-[1,2,3]triazol-4-yl]-2-methyl-phenol; (Yield 0.75 g, 59%); and 1-(4-chloro-benzyl)-4-(3-methoxymethoxy-4-methyl-phenyl)-1H[1,2,3]triazole. (Yield 0.61 g, 21%).

Example 35

4-Chloro-3-{5-[1-(4-chloro-benzyl)-1H-[1,2,3]triazol-4-yl]-2-methyl-phenoxymethyl}-thieno[3,2-c]pyridine-7-carboxylic acid ethyl ester

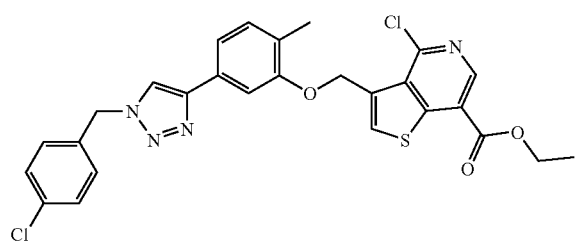

M.W. 553.471  $C_{27}H_{22}Cl_2N_4O_3S$

A suspension of cesium carbonate (1.11 g, 3.41 mmol), 5-[1-(4-chloro-benzyl)-1H-[1,2,3]triazol-4-yl]-2-methyl-phenol (0.75 g, 2.50 mmol) (from Example 34 supra) in tetrahydrofuran-N,N-dimethylformamide (5:2, 23 mL) was heated at 70° C. for 2 hours. 3-Bromomethyl-4-chloro-thieno[3,2-c]pyridine-7-carboxylic acid ethyl ester (0.76 g, 2.27 mmol) (from Example 1 supra) was added. Heating was continued for 18 hours. The reaction mixture was partitioned between ethyl acetate and water. The precipitate was filtered, washed with ethyl acetate and dried to give 4-chloro-3-{5-[1-(4-chloro-benzyl)-1H-[1,2,3]triazol-4-yl]-2-methyl-phenoxymethyl}-thieno[3,2-c]pyridine-7-carboxylic acid ethyl ester as a white powder. (Yield 0.33 g, 26%).

Example 36

4-Amino-3-{5-[1-(4-chloro-benzyl)-1H-[1,2,3]triazol-4-yl]-2-methyl-phenoxymethyl}-thieno[3,2-c]pyridine-7-carboxylic acid ethyl ester

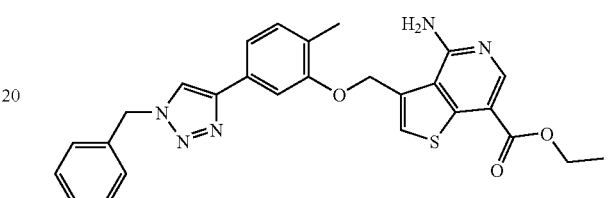

M.W. 534.041  $C_{27}H_{24}ClN_5O_3S$

Ammonia gas was bubbled into a solution of 4-chloro-3-{5-[1-(4-chloro-benzyl)-1H-[1,2,3]triazol-4-yl]-2-methyl-phenoxymethyl}-thieno[3,2-c]pyridine-7-carboxylic acid ethyl ester (0.33 g, 0.60 mmol) (from Example 35 supra) in 2-propanol (30 mL) for 20 minutes. The mixture was heated in a microwave reactor at 140° C. for 2 hours. The reaction mixture was concentrated. The residue washed with hot methanol, filtered and dried to give 4-amino-3-{5-[1-(4-chloro-benzyl)-1H-[1,2,3]triazol-4-yl]-2-methyl-phenoxymethyl}-thieno[3,2-c]pyridine-7-carboxylic acid ethyl ester as a white powder. (Yield 0.23 g, 72%).

Example 37

4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide

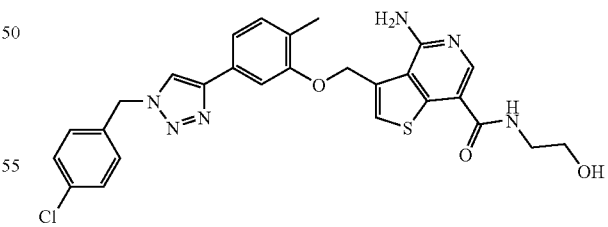

M.W. 549.056  $C_{27}H_{25}ClN_6O_3S$

A solution of 4-amino-3-{5-[1-(4-chloro-benzyl)-1H-[1,2,3]triazol-4-yl]-2-methyl-phenoxymethyl}-thieno[3,2-c]pyridine-7-carboxylic acid ethyl ester (0.050 g, 0.09 mmol) (from Example 36 supra) in dimethylsulfoxide (0.5 mL) was treated with ethanolamine (1.5 mL) (Aldrich) and heated at 160° C. for 2 hours in a microwave reactor. The precipitate was filtered, washed with methanol and dried to give 4-amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide as a white powder. (Yield 34.5 mg, 68%).

HRMS (ES+) m/z Calcd for $C_{27}H_{25}ClN_6O_3S+H$ [(M+H)+]: 549.1470. Found: 549.1459.

Example 38

4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide toluene-4-sulfonic acid salt

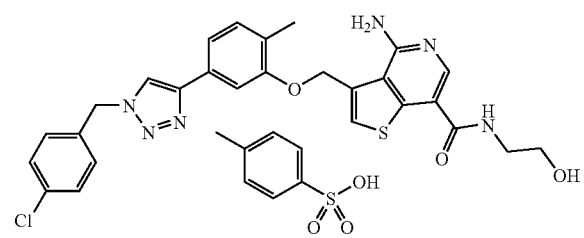

M.W. 549.056 + 172.204    $C_{27}H_{25}ClN_6O_3S \cdot C_7H_8O_3S$

To solution of 4-amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide (0.159 g, 0.29 mmol) (from Example 37 supra) in methanol (10 mL) was treated with toluene-4-sulfonic acid hydrate (61.0 mg, 0.319 mmol) and heated at room temperature for 40 minutes. The solution was concentrated. The residue washed with diethyl ether, dissolved in water and lyophilized to 4-amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide 1.5 toluene-4-sulfonic acid salt. (Yield 0.21 g, 100%).

HRMS (ES+) m/z Calcd for $C_{27}H_{25}ClN_6O_3S+H$ [(M+H)+]: 549.1470. Found: 549.1467.

Example 39

3-Hydroxy-4-methyl-benzoic acid N'-[2-(4-chloro-phenyl)-acetyl]-hydrazide

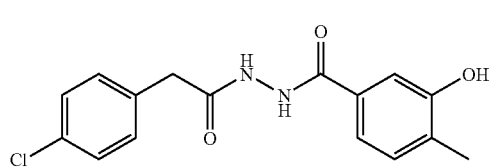

M.W. 318.76    $C_{16}H_{15}ClN_2O_3$

A mixture of 4-chlorophenylacetyl chloride (1.36 g, 7.22 mmol) (Aldrich), 3-hydroxy-4-methyl-benzoic acid hydrazide (1.0 g, 6.02 mmol) (from Example 6 supra) and triethylamine (1.36 mL) in tetrahydrofuran (20 mL) was heated at 85° C. for 1 day. The reaction mixture was partitioned between ethyl acetate and water. The aqueous phase was extracted with ethyl acetate (1×). The combined organic phase washed with water and brine, dried (magnesium sulfate) and concentrated. The residue washed with ethyl acetate and dichloromethane and dried to give 3-hydroxy-4-methyl-benzoic acid N'-[2-(4-chloro-phenyl)-acetyl]-hydrazide. (Yield 0.91 g, 95%).

Example 40

5-[5-(4-Chloro-benzyl)-[1,3,4]-oxadiazol-2-yl]-2-methyl-phenol

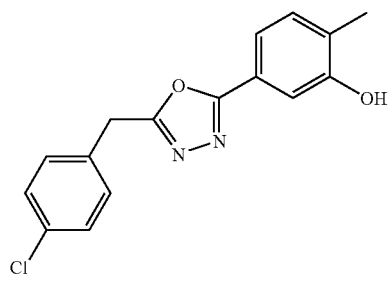

M.W. 300.75    $C_{16}H_{16}ClN_2O_2$

To a solution of 3-hydroxy-4-methyl-benzoic acid N'-[2-(4-chloro-phenyl)-acetyl]-hydrazide (0.91 g, 2.85 mmol) (from Example 39 supra) in acetonitrile (20 mL) was added diisopropylethylamine (3.0 mL, 17.1 mmol) and triphenylphosphine (1.50 g, 5.70 mmol). After stirring 5 minutes, hexachloroethane (1.01 g, 4.28 mmol) (Aldrich) was added and the mixture was allowed to stir for 2 days at room temperature. The solvent was evaporated. The residue was partitioned between ethyl acetate and water. The aqueous phase was extracted with ethyl acetate (1×). The combined organic phase was washed with water and brine, dried (magnesium sulfate) and concentrated. The residue was purified by flash chromatography eluting with 20% ethyl acetate in hexanes to 5-[5-(4-chloro-benzyl)-[1,3,4]-oxadiazol-2-yl]-2-methyl-phenol. (Yield 0.68 g, 79%).

Example 41

4-Chloro-3-{5-[5-(4-chloro-benzyl)-[1,3,4]oxadiazol-2-yl]-2-methyl-phenoxymethyl}-thieno[3,2-c]pyridine-7-carboxylic acid ethyl ester

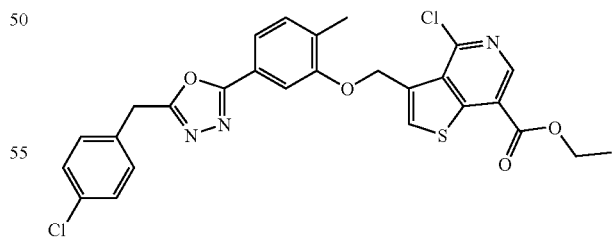

M.W. 554.46    $C_{27}H_{21}Cl_2N_3O_4S$

A suspension of cesium carbonate (0.54 g, 1.66 mmol), 5-[5-(4-chloro-benzyl)-[1,3,4]-oxadiazol-2-yl]-2-methyl-phenol (0.36 g, 1.20 mmol) (from Example 40 supra) in tetrahydrofuran/N,N-dimethylformamide (5:2, 21 mL) was heated at 68° C. for 2 hours. 3-Bromomethyl-4-chloro-thieno[3,2-c]pyridine-7-carboxylic acid ethyl ester (0.36 g, 1.08 mmol) (from Example 1 supra) was added. Heating was continued for 2 hours. The reaction mixture was partitioned between ethyl acetate and water. The aqueous phase was extracted with ethyl acetate (2×). The combined organic phase washed with water and brine, dried (magnesium sulfate) and concentrated. The residue washed with ethyl acetate and dried to give 4-chloro-3-{5-[5-(4-chloro-benzyl)-[1,3,4]oxadiazol-2-yl]-2-methyl-phenoxymethyl}-thieno[3,2-c]pyridine-7-carboxylic acid ethyl ester. (Yield 0.17 g, 26%).

Example 42

4-Amino-3-{5-[5-(4-chloro-benzyl)-[1,3,4]oxadiazol-2-yl]-2-methyl-phenoxymethyl}-thieno[3,2-c]pyridine-7-carboxylic acid ethyl ester

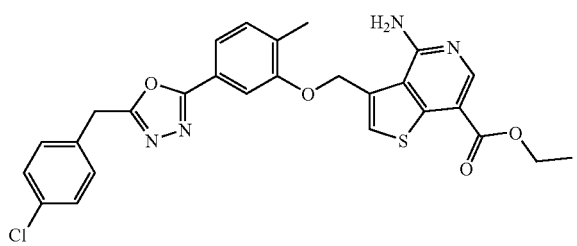

M.W. 535.03   $C_{27}H_{23}ClN_4O_4S$

Ammonia gas was bubbled into a solution of 4-chloro-3-{5-[5-(4-chloro-benzyl)-[1,3,4]oxadiazol-2-yl]-2-methyl-phenoxymethyl}-thieno[3,2-c]pyridine-7-carboxylic acid ethyl ester (0.11 g, 0.20 mmol) (from Example 41 supra) in 2-propanol (15 mL) for 20 min. The mixture was heated in a microwave reactor at 140° C. for 5.5 hours. The reaction mixture was concentrated. The residue was washed with hot methanol, filtered and dried to give 4-amino-3-{5-[5-(4-chloro-benzyl)-[1,3,4]oxadiazol-2-yl]-2-methyl-phenoxymethyl}-thieno[3,2-c]pyridine-7-carboxylic acid ethyl ester. (Yield 0.07 g, 64%).

Example 43

4-Amino-3-{5-[5-(4-chloro-benzyl)-[1,3,4]oxadiazol-2-yl]-2-methyl-phenoxymethyl}-thieno[3,2-c]pyridine-7-carboxylic acid (2-hydroxy-ethyl)-amide

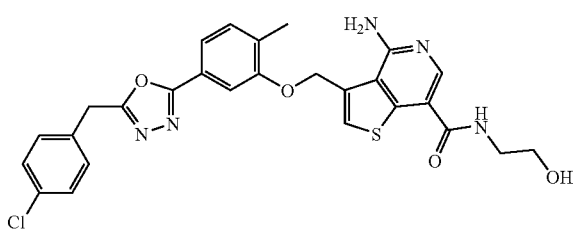

M.W. 550.037   $C_{27}H_{24}ClN_5O_4S$

A solution of 4-amino-3-{5-[5-(4-chloro-benzyl)-[1,3,4]oxadiazol-2-yl]-2-methyl-phenoxymethyl}-thieno[3,2-c]pyridine-7-carboxylic acid ethyl ester (0.07 g, 0.13 mmol) (from Example 42 supra) in dimethylsulfoxide (0.5 mL) was treated with ethanolamine (1.5 mL) and heated at 160° C. for 2.8 hours in a microwave reactor. The reaction mixture was purified by C18 column chromatography and SFC column chromatography to give 4-amino-3-{5-[5-(4-chloro-benzyl)-[1,3,4]oxadiazol-2-yl]-2-methyl-phenoxymethyl}-thieno[3,2-c]pyridine-7-carboxylic acid (2-hydroxy-ethyl)-amide as a white powder. (Yield 8 mg, 11%).

HRMS (ES⁺) m/z Calcd for $C_{27}H_{24}ClN_5O_4S+H$ [(M+H)⁺]: 550.1311. Found: 550.1311.

Example 44

3-Hydroxy-4-methyl-benzoic acid N'-(4-chloro-benzoyl)-hydrazide

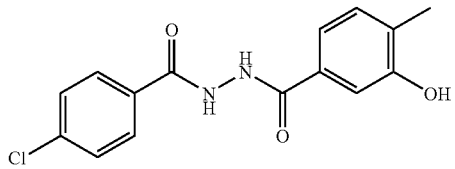

M.W. 304.74   $C_{15}H_{13}ClN_2O_3$

A mixture of 4-chlorobenzoyl chloride (0.92 mL, 7.22 mmol) (Aldrich), 3-hydroxy-4-methyl-benzoic acid hydrazide (1.0 g, 6.02 mmol) (from Example 6 supra) and triethylamine (1.36 mL) in tetrahydrofuran (20 mL) was heated at 85° C. for 1 day. The reaction mixture was partitioned between ethyl acetate and water. The precipitate washed with ethyl acetate and dichloromethane and dried to give 3-hydroxy-4-methyl-benzoic acid N'-(4-chloro-benzoyl)-hydrazide. (Yield 1.28 g, 70%).

Example 45

5-[5-(4-Chloro-phenyl)-[1,3,4]-oxadiazol-2-yl]-2-methyl-phenol

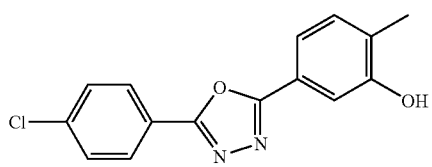

M.W. 286.72   $C_{15}H_{11}ClN_2O_2$

To a solution of 3-hydroxy-4-methyl-benzoic acid N'-(4-chloro-benzoyl)-hydrazide (1.28 g, 4.20 mmol) (from Example 44 supra) in acetonitrile (20 mL) was added diisopropylethylamine (4.4 mL, 25.2 mmol) and triphenylphosphine (2.21 g, 8.40 mmol). After stirring 5 minutes, hexachloroethane (1.49 g, 6.30 mmol) (Aldrich) was added and the mixture was allowed to stir for 1 day at room temperature. The solvent was evaporated. The residue was partitioned between ethyl acetate and water. The aqueous phase was extracted with ethyl acetate (1×). The combined organic phase washed with water and brine, dried (magnesium sulfate) and concentrated. The residue was purified by flash chromatography eluting with 0-60% ethyl acetate in hexanes to give 5-[5-(4-chloro-phenyl)-[1,3,4]-oxadiazol-2-yl]-2-methyl-phenol. (Yield 0.34 g, 28%).

Example 46

4-Chloro-3-{5-[5-(4-chloro-phenyl)-[1,3,4]oxadiazol-2-yl]-2-methyl-phenoxy-methyl}-thieno[3,2-c]pyridine-7-carboxylic acid ethyl ester

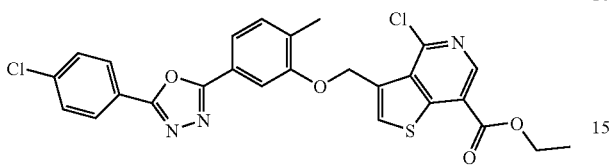

M.W. 540.43    $C_{26}H_{19}Cl_2N_3O_4S$

A suspension of cesium carbonate (0.54 g, 1.66 mmol), 5-[5-(4-chloro-benzyl)-[1,3,4]-oxadiazol-2-yl]-2-methyl-phenol (0.34 g, 1.19 mmol) (from Example 45 supra) in tetrahydrofuran/N,N-dimethylformamide (5:2, 21 mL) was heated at 68° C. for 2 hours. 3-Bromomethyl-4-chloro-thieno[3,2-c]pyridine-7-carboxylic acid ethyl ester (0.36 g, 1.08 mmol) (from Example 1 supra) was added. Heating was continued for 2 hours. The reaction mixture was partitioned between ethyl acetate and water. The aqueous phase was extracted with ethyl acetate (2×). The combined organic phase washed with water and brine, dried (magnesium sulfate) and concentrated. The residue washed with ethyl acetate and dried to give 4-chloro-3-{5-[5-(4-chloro-phenyl)-[1,3,4]oxadiazol-2-yl]-2-methyl-phenoxymethyl}-thieno[3,2-c]pyridine-7-carboxylic acid ethyl ester. (Yield 0.30 g, 47%).

Example 47

4-Amino-3-{5-[5-(4-chloro-phenyl)-[1,3,4]oxadiazol-2-yl]-2-methyl-phenoxy-methyl}-thieno[3,2-c]pyridine-7-carboxylic acid ethyl ester

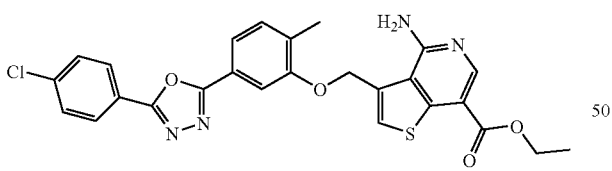

M.W. 521.00    $C_{26}H_{21}ClN_4O_4S$

Ammonia gas was bubbled into a solution of 4-chloro-3-{5-[5-(4-chloro-phenyl)-[1,3,4]oxadiazol-2-yl]-2-methyl-phenoxymethyl}-thieno[3,2-c]pyridine-7-carboxylic acid ethyl ester (0.30 g, 0.56 mmol) (from Example 46 supra) in 2-propanol (30 mL) for 20 minutes. The mixture was heated in a microwave reactor at 140° C. for 5.5 hours. The reaction mixture was concentrated. The residue washed with hot methanol, filtered and dried to give 4-amino-3-{5-[5-(4-chloro-phenyl)-[1,3,4]oxadiazol-2-yl]-2-methyl-phenoxymethyl}-thieno[3,2-c]pyridine-7-carboxylic acid ethyl ester. (Yield 0.22 g, 76%).

Example 48

4-Amino-3-{5-[5-(4-chloro-phenyl)-[1,3,4]oxadiazol-2-yl]-2-methyl-phenoxy-methyl}-thieno[3,2-c]pyridine-7-carboxylic acid

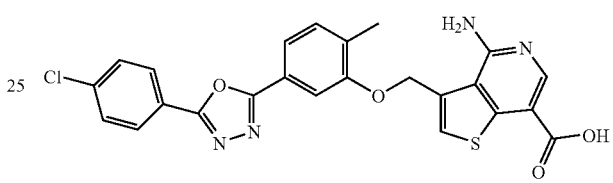

M.W. 492.94    $C_{24}H_{17}ClN_4O_4S$

An aqueous solution of sodium hydroxide (2 N, 2.0 mL, 1.0 mmol) was added to a solution of 4-amino-3-{5-[5-(4-chloro-phenyl)-[1,3,4]oxadiazol-2-yl]-2-methyl-phenoxymethyl}-thieno[3,2-c]pyridine-7-carboxylic acid ethyl ester (0.22 g, 0.42 mmol) (from Example 47 supra) in tetrahydrofuran/methanol (3:1, 8 mL) and the mixture was heated at 50° C. for 1 day. The reaction mixture was concentrated and azeotroped with toluene. The solid residue was triturated with ethyl acetate. The solid was then suspended in water and treated with hydrochloric acid (1 N). After stirring 30 minutes, the solid was collected, washed with water and dried to give 4-amino-3-{5-[5-(4-chloro-phenyl)-[1,3,4]oxadiazol-2-yl]-2-methyl-phenoxymethyl}-thieno[3,2-c]pyridine-7-carboxylic acid. (Yield 0.20 g, 95%).

Example 49

4-Amino-3-{5-[5-(4-chloro-phenyl)-[1,3,4]oxadiazol-2-yl]-2-methyl-phenoxy-methyl}-thieno[3,2-c]pyridine-7-carboxylic acid (2-hydroxy-ethyl)-amide trifluoroacetic acid salt

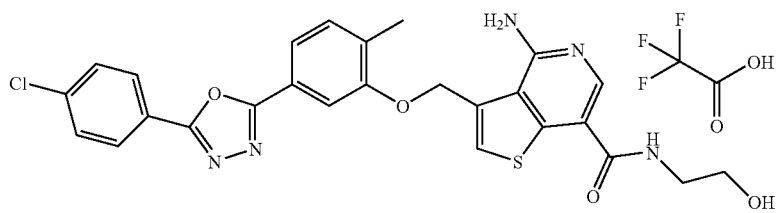

M.W. 650.032    $C_{26}H_{22}ClN_5O_4S \cdot C_2HF_3O_2$

A mixture of 4-amino-3-{5-[5-(4-chloro-phenyl)-[1,3,4]oxadiazol-2-yl]-2-methyl-phenoxymethyl}-thieno[3,2-c]pyridine-7-carboxylic acid (0.10 g, 0.20 mmol) (from Example 48 supra), 1-hydroxybenzotriazole hydrate (43 mg, 0.32 mmol) (Aldrich) and 1,3-diisopropylcarbodiimide (0.044 mL, 0.17 mmol) (Aldrich) were combined in tetrahydrofuran/N,N-dimethylformamide (3.6 mL, 5:1) with stirring. After 1 hour, ethanolamine (0.036 mL, 0.60 mmol) (Aldrich) was added. The mixture was stirred at room temperature for 18 hours and then concentrated. The residue was purified by HPLC eluting with acetonitrile/water to give 4-amino-3-{5-[5-(4-chloro-phenyl)-[1,3,4]oxadiazol-2-yl]-2-methyl-phenoxymethyl}-thieno[3,2-c]pyridine-7-carboxylic acid (2-hydroxy-ethyl)-amide trifluoro-acetic acid salt as a white powder. (Yield 52 mg, 40%).

HRMS (ES⁺) m/z Calcd for $C_{26}H_{22}ClN_5O_4S+H$ [(M+H)⁺]: 536.1154. Found: 536.1149.

Example 50

3-Methoxymethoxy-4-methyl-benzoic acid

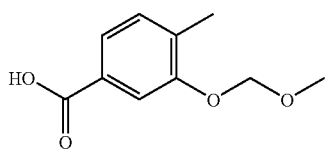

$C_{10}H_{12}O_4$   M.W. 196.205

A solution of 3-methoxymethoxy-4-methyl-benzoic acid ethyl ester (4.5 g, 20 mmol) (from Example 3 supra) in a mixture of ethanol (50 mL), water (20 mL) and 1 N aqueous sodium hydroxide (30 mL) was stirred at room temperature for 18 hours. Mixture was concentrated to remove most of the ethanol. Resulting aqueous solution was acidified with acetic acid (2.5 g, 41.6 mmol). After standing for another 30 minutes, the precipitate formed was collected by filtration, washed with water and dried to give 3-methoxymethoxy-4-methyl-benzoic acid as a white powder. (Yield 3.82 g, 97%).

Example 51

5-(3-Methoxymethoxy-4-methyl-phenyl)-3-methyl-[1,2,4]oxadiazole

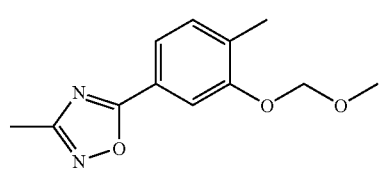

M.W. 234.257   $C_{12}H_{14}N_2O_3$

A mixture of 3-methoxymethoxy-4-methyl-benzoic acid (1.96 g, 10 mmol) (from Example 50 supra), 1-(3-dimethylaminopropyl)-3-ethylcarbodiimide (1.92 g, 10 mmol) (Aldrich) and 1-hydroxybenzotriazole hydrate (1.35 g, 10 mmol) (Aldrich) in N,N-dimethylformamide (25 mL) was stirred at room temperature for 30 minutes. Acetamide oxime (0.74 g, 10 mmol) (GFS Chemicals) was added and mixture heated at 140 C for 2 hours. After cooling, mixture was partitioned between ethyl acetate (2×) and saturated aqueous bicarbonate solution. Ethyl acetate solutions were combined and concentrated and residue purified by flash chromatography to give 5-(3-methoxymethoxy-4-methyl-phenyl)-3-methyl-[1,2,4]oxadiazole. (Yield 1.23 g, 52.5%).

Example 52

2-Methyl-5-(3-methyl-[1,2,4]oxadiazol-5-yl)-phenol

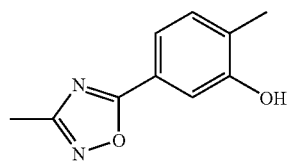

M.W. 190.20   $C_{10}H_{10}N_2O$

To a solution of 5-(3-methyloxymethoxy-4-methyl-phenyl)-3-methyl-[1,2,4]oxadiazole (1.23 g, 5.25 mmol) (from Example 51 supra) in tetrahydrofuran/2-propanol (1:1, 30 mL) was added 13.1 mL of 4M HCl in dioxane (Aldrich). The reaction mixture was stirred at room temperature for 18 hours. The solution was concentrated. The residue was diluted with ethyl acetate, washed with water and brine, dried (magnesium sulfate) and concentrated. The residue was recrystallized from ethyl acetate/hexanes and dried to give 2-methyl-5-(3-methyl-[1,2,4]oxadiazol-5-yl)-phenol. (Yield 0.88 g, 88%).

Example 53

4-Chloro-3-[2-methyl-5-(3-methyl-[1,2,4]oxadiazol-5-yl)-phenoxymethyl]-thieno[3,2-c]pyridine-7-carboxylic acid ethyl ester

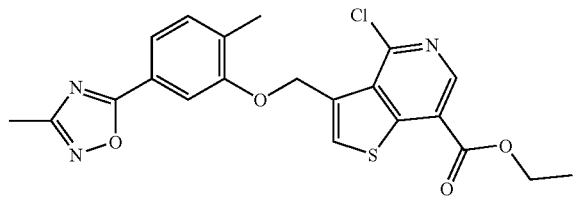

M.W. 443.91   $C_{21}H_{18}ClN_3O_4S$

A suspension of cesium carbonate (1.02 g, 3.13 mmol), 2-methyl-5-(3-methyl-[1,2,4]oxadiazol-5-yl)-phenol (0.42 g, 2.20 mmol) (from Example 52 supra) in tetrahydrofuran/N,N-dimethylformamide (5:2, 21 mL) was heated at 70° C. for 2 hours. 3-Bromomethyl-4-chloro-thieno[3,2-c]pyridine-7-carboxylic acid ethyl ester (0.68 g, 2.04 mmol) (from Example 1 supra) was added. Heating was continued for 1 hour. The reaction mixture was partitioned between dichloromethane and water. The aqueous phase was extracted with dichloromethane (2×). The combined organic phase washed with water and brine, dried (magnesium sulfate) and concentrated. The residue was purified by flash chromatography eluting with 5-10% ethyl acetate in dichloromethane to give 4-chloro-3-[2-methyl-5-(3-methyl-[1,2,4]oxadiazol-5-yl)- phenoxymethyl]-thieno[3,2-c]pyridine-7-carboxylic acid ethyl ester. (Yield 0.51 g, 57%).

Example 54

4-Amino-3-[2-methyl-5-(3-methyl-[1,2,4]oxadiazol-5-yl)-phenoxymethyl]-thieno[3,2-c]pyridine-7-carboxylic acid ethyl ester

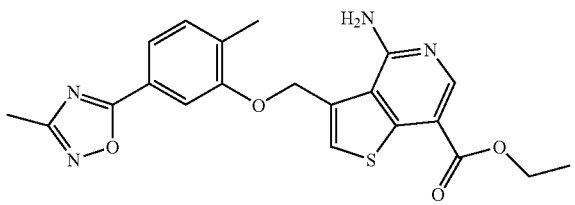

M.W. 424.48   $C_{21}H_{20}N_4O_4S$

Ammonia gas was bubbled into a solution of 4-chloro-3-[2-methyl-5-(3-methyl-[1,2,4]oxadiazol-5-yl)-phenoxymethyl]-thieno[3,2-c]pyridine-7-carboxylic acid ethyl ester (0.42 g, 0.95 mmol) (from Example 53 supra) in 2-propanol (30 mL) for 20 minutes. The mixture was heated in a microwave reactor at 140° C. for 2 hours. The reaction mixture was concentrated. The residue washed with hot methanol, filtered and dried to give 4-amino-3-[2-methyl-5-(3-methyl-[1,2,4]oxadiazol-5-yl)-phenoxymethyl]-thieno[3,2-c]pyridine-7-carboxylic acid ethyl ester as a white powder. (Yield 0.33 g, 83%).

Example 55

4-Amino-3-[2-methyl-5-(3-methyl-[1,2,4]oxadiazol-5-yl)-phenoxymethyl]-thieno[3,2-c]pyridine-7-carboxylic acid

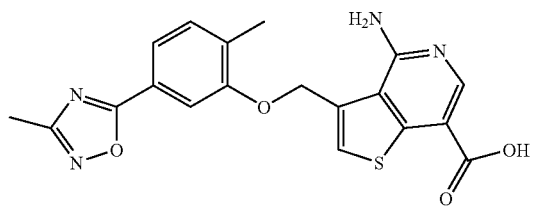

M.W. 396.43   $C_{19}H_{16}N_4O_4S$

An aqueous solution of sodium hydroxide (2 N, 3.0 mL, 1.5 mmol) was added to a solution of 4-amino-3-[2-methyl-5-(3-methyl-[1,2,4]oxadiazol-5-yl)-phenoxymethyl]-thieno[3,2-c]pyridine-7-carboxylic acid ethyl ester (0.33 g, 0.78 mmol) (from Example 54 supra) in tetrahydrofuran/methanol (3:1, 8 mL) and the mixture was heated at 50° C. for 1 day. The reaction mixture was concentrated and azeotroped with toluene. The solid residue was triturated with ethyl acetate. The solid was then suspended in water and treated with hydrochloric acid (1N). After stirring 30 minutes, the solid was collected, washed with water and dried to 4-amino-3-[2-methyl-5-(3-methyl-[1,2,4]oxadiazol-5-yl)-phenoxymethyl]-thieno[3,2-c]pyridine-7-carboxylic acid. (Yield 0.29 g, 94%).

Example 56

4-Amino-3-[2-methyl-5-(3-methyl-[1,2,4]oxadiazol-5-yl)-phenoxymethyl]-thieno-[3,2-c]pyridine-7-carboxylic acid (2-hydroxy-ethyl)-amide trifluoroacetic acid salt

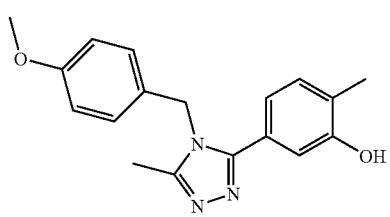

M.W. 553.516   $C_{21}H_{21}N_5O_4S \cdot C_2HF_3O_2$

A mixture of 4-amino-3-[2-methyl-5-(3-methyl-[1,2,4]oxadiazol-5-yl)-phenoxymethyl]-thieno[3,2-c]pyridine-7-carboxylic acid (0.10 g, 0.25 mmol) (from Example 55 supra), 1-hydroxybenzotriazole hydrate (54 mg, 0.40 mmol) (Aldrich) and 1,3-diisopropylcarbodiimide (0.055 mL, 0.36 mmol) (Aldrich) were combined in tetrahydrofuran/N,N-dimethylformamide (3.6 mL, 5:1) with stirring. After 1 hour, ethanolamine (0.046 mL, 0.76 mmol) (Aldrich) was added. The mixture was stirred at room temperature for 18 hours and then concentrated. The residue was purified by HPLC eluting with acetonitrile/water to give 4-amino-3-[2-methyl-5-(3-methyl-[1,2,4]oxadiazol-5-yl)-phenoxymethyl]-thieno[3,2-c]pyridine-7-carboxylic acid (2-hydroxy-ethyl)-amide trifluoro-acetic acid salt as a white powder. (Yield 70 mg, 50%).

HRMS (ES$^+$) m/z Calcd for $C_{21}H_{21}N_5O_4S$+H [(M+H)$^+$]: 440.1387. Found: 440.1384.

Example 57

5-[4-(4-Methoxy-benzyl)-5-methyl-4H-[1,2,4]triazol-3-yl]-2-methyl-phenol

M.W. 309.37   $C_{18}H_{19}N_3O_2$

A mixture of 2-methyl-5-(5-methyl-[1,3,4]oxadiazol-2-yl)-phenol (0.65 g; 3.42 mmol) (from Example 11 supra) and 4-methoxybenzylamine (3.10 g; 22.6 mmol) (Aldrich) in a sealed reaction vessel was heated in an oil bath at 150-155° C. for 42 hours. The reaction mixture was cooled to room temperature and diluted with dichloromethane and hexanes, forcing the product to precipitate out of solution. The crude solid was collected by filtration and then precipitated again from a dichloromethane-methanol solution as the solvent was evaporated off. The solid was collected and dried, to give 5-[4-(4-methoxy-benzyl)-5-methyl-4H-[1,2,4]triazol-3-yl]-2-methyl-phenol. (Yield 0.849 g; 76.3%).

Example 58

4-Chloro-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester

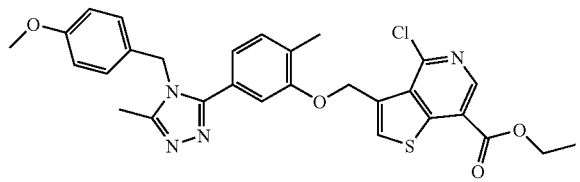

M.W. 563.08  $C_{29}H_{27}ClN_4O_4S$

Potassium carbonate (0.246 g; 1.67 mmol) was added to a solution of 5-[4-(4-methoxy-benzyl)-5-methyl-4H-[1,2,4]triazol-3-yl]-2-methyl-phenol (0.17 g; 0.55 mmol) (from Example 57 supra) DMF (3.4 mL) and the mixture was stirred at room temperature for 5 minutes. 3-Bromomethyl-4-chloro-thieno[3,2-c]pyridine-7-carboxylic acid ethyl ester (0.246 g; 0.74 mmol) (from Example 1 supra) was then added neat and stirring continued at room temperature for 4.25 hours. The dark red mixture was diluted with ethyl acetate and the mixture was washed twice with water and then once with brine. The organic phase was dried over sodium sulfate and concentrated. The crude material was purified by flash chromatography (80 g column, eluting with 4% methanol in dichloromethane followed by a gradient to 40% methanol). The product-containing fractions were combined and concentrated. A small contaminant was then removed from the chromatographed material by concentrating a dichloromethane-hexanes solution of the material to a small volume, resulting in precipitation of the product as a white solid which was then collected by filtration and dried to give 4-chloro-3-{5-[4-(4-methoxy-benzyl)-5-methyl-4H-[1,2,4]triazol-3-yl]-2-methyl-phenoxy-methyl}-thieno[3,2-c]pyridine-7-carboxylic acid ethyl ester. (Yield 0.188 g; 60.8%).

Example 59

4-Amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester

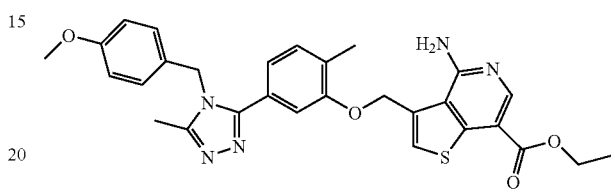

M.W. 543.65  $C_{29}H_{29}N_5O_4S$

Ammonia gas was bubbled into a suspension of 4-chloro-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester (0.330 g; 0.59 mmol) (from Example 58 supra) in 2-propanol (20 mL) for 15-20 minutes. The mixture was then heated in a microwave reactor at 140° C. for 90 minutes. The reaction mixture was concentrated and the residue was purified by flash chromatography (120 g column; 4% methanol in dichloromethane followed by a gradient to 40% methanol) to give 4-amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester (0.263 g; 96% pure; 78.72%).

Example 60

4-Amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid (2-hydroxy-ethyl)-amide

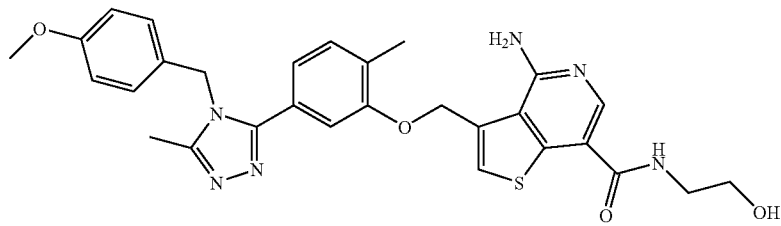

M.W. 558.66  $C_{29}H_{30}N_6O_4S$

Ethanolamine (1.8 mL; 29.9 mmol) (Aldrich) was added to a solution of 4-amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester (50 mg; 0.08277 mmole) (from Example 59 supra) in dimethylsulfoxide (0.6 mL). The mixture was heated in a microwave reactor at 135° C. for 2.25 hours. After cooling to room temperature, the reaction mixture was diluted with water, resulting in precipitation of the product as a milky solid which was collected by centrifugation and dried. The crude solid was triturated with hot methanol, cooled slightly, filtered and dried, to give 4-amino-3-{5-[4-(4-methoxy-benzyl)-5-methyl-4H-[1,2,4]triazol-3-yl]-2-methyl-phenoxymethyl}-thieno[3,2-c]pyridine-7-carboxylic acid (2-hydroxy-ethyl)-amide in two crops. (Yield 31.2 mg, 51.3%). HRMS (ES$^+$) m/z Calcd for $C_{29}H_{30}N_6O_4S$+H [(M+H)$^+$]: 559.2122. Found: 559.2120.

Example 61

4-Chloro-3-[2-methyl-5-(methyl-4H-[1,2,4]triazol-3-yl)-phenoxymethyl]-thieno[3,2-c]pyridine-7-carboxylic acid ethyl ester

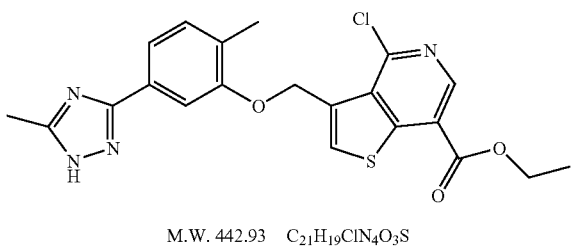

M.W. 442.93   $C_{21}H_{19}ClN_4O_3S$

A mixture of 4-chloro-3-{5-[4-(4-methoxy-benzyl)-5-methyl-4H-[1,2,4]triazol-3-yl]-2-methyl-phenoxymethyl}-thieno[3,2-c]pyridine-7-carboxylic acid ethyl ester (85 mg; 0.151 mmol) (from Example 58 supra) with trifluoroacetic acid (1.0 mL; 13 mmol), anisole (100 µL; 0.92 mmol) (Aldrich) and sulfuric acid (50 µL; 0.94 mmol) was stirred at room temperature for 42 hours. The mixture was concentrated. The residue was diluted with dichloromethane and concentrated again. The residue was then diluted with dichloromethane and methanol and washed with saturated aqueous sodium bicarbonate solution and water. The aqueous phases were backwashed with a mixture of dichloromethane and methanol. The two organic phases were combined, dried over sodium sulfate and concentrated. The crude material was purified by flash chromatography (12 g column; EtOAc followed by a gradient to 60:40 EtOAc: methanol) to give 4-chloro-3-[2-methyl-5-(methyl-4H-[1,2,4]triazol-3-yl)-phenoxymethyl]-thieno[3,2-c]pyridine-7-carboxylic acid ethyl ester. (Yield 56.3 mg, 84.20%).

Example 62

4-Amino-3-[2-methyl-5-(5-methyl-4H-[1,2,4]triazol-3-yl)-phenoxymethyl]-thieno[3,2-c]pyridine-7-carboxylic acid ethyl ester

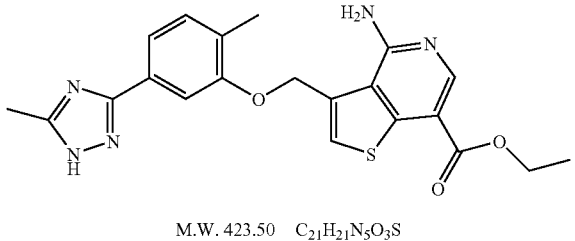

M.W. 423.50   $C_{21}H_{21}N_5O_3S$

Ammonia gas was bubbled into a suspension of 4-chloro-3-[2-methyl-5-(methyl-4H-[1,2,4]triazol-3-yl)-phenoxymethyl]-thieno[3,2-c]pyridine-7-carboxylic acid ethyl ester (0.106 g; 0.24 mmol) (from Example 61 supra) in 2-propanol (20 mL) for 15-20 minutes. The mixture was then heated in a microwave reactor at 140° C. for 75 minutes. After cooling to room temperature the reaction mixture was diluted with dichloromethane (~75 mL) and washed with water and then brine. The organic phase was dried ($Na_2SO_4$) and concentrated. The residue was triturated twice with hot dichloromethane to give 4-amino-3-[2-methyl-5-(5-methyl-4H-[1,2,4]triazol-3-yl)-phenoxymethyl]-thieno[3,2-c]pyridine-7-carboxylic acid ethyl ester as a white solid. (Yield 80.4 mg) Additional product was obtained by chromatographing the mother liquors from the two triturations. (Yield 7.7 mg, overall 82.49%).

HRMS (ES$^+$) m/z Calcd for $C_{21}H_{21}N_5O_3S+H$ [(M+H)$^+$]: 424.1438. Found: 424.1433.

Example 63

4-Amino-3-[2-methyl-5-(5-methyl-4H-[1,2,4]triazol-3-yl)-phenoxymethyl]-thieno[3,2-c]pyridine-7-carboxylic acid (2-hydroxy-ethyl)-amide

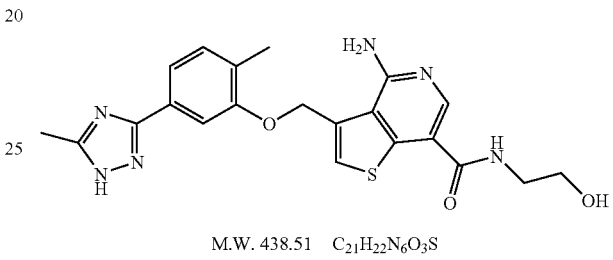

M.W. 438.51   $C_{21}H_{22}N_6O_3S$

Ethanolamine (1.5 mL; 24.9 mmol) (Aldrich) was added to a suspension of 4-amino-3-[2-methyl-5-(5-methyl-4H-[1,2,4]triazol-3-yl)-phenoxymethyl]-thieno[3,2-c]pyridine-7-carboxylic acid ethyl ester (68.4 mg; 0.162 mmol) (from Example 62 supra) in dimethylsulfoxide (0.5 mL). The mixture was heated in a microwave reactor at 135° C. for 90 minutes and then for 1 hour at 140° C. The crude reaction mixture was concentrated under high vacuum with heat to remove most of the ethanolamine and DMSO. The residue was diluted with water, causing a milky precipitate to drop out of solution. The solid was collected by filtration, washed with water and dried. The material was then triturated with hot methanol to give 4-amino-3-[2-methyl-5-(5-methyl-4H-[1,2,4]triazol-3-yl)-phenoxymethyl]-thieno[3,2-c]pyridine-7-carboxylic acid (2-hydroxy-ethyl)-amide as an off-white solid. (Yield 48 mg, 67.8%).

HRMS (ES$^+$) m/z Calcd for $C_{21}H_{22}N_6O_3S+H$ [(M+H)$^+$]: 439.1547. Found: 439.1544.

Example 64

Kinase Enzyme Inhibition Assay (IC$_{50}$)

c-Raf HTRF Assay with 6H-MEK as Substrate (Dose Response)

Assay Principle:

The assay utilizes 6H-MEK as the substrate. Upon c-Raf phosphorylation, phosphorylated 6H-MEK is detected with rabbit anti-phospho-MEK1/2, Eu-labeled anti-rabbit, and APC-labeled anti-6H antibodies.

Reagents and Instruments:

Enzyme: cloned human c-Raf with EE-tag; phosphorylated (co-expressed with v-src-FLAG in baculovirus Hi5 cells), 0.2 mg/mL (2.74 µM assuming a molecular weight of 73 kD) stored at −15° C.

Substrate: WT full-length 6H-MEK, 4.94 mg/mL (154.4 µM assuming a MW of 32 kD) stored at −15° C.

Antibodies: Rabbit (α-P-(Ser 217/221)-MEK-1/2 Ab (from Cell Signaling, Cat. #9121B, Lot 14); Eu-(α-rabbit IgG (from Wallac, Cat. # AD0083, Lot 318663, 710 ug/mL, 4.4 µM); (α-6H-SureLight-APC (from Martek, Cat. #AD0059H, Lot E012AB01, 3.03 µM).
Reader: Envision from PerkinElmer, HTRF reading mode with 412 mirror
Assay Plate Matrix all-black polypropylene plates (Cat. #4344)
Others: Weidman 384 polypropylene plates (REMP) for compound plate.
Assay Procedure:
(1) Prepare Kinase Assay Buffer (KAB): 50 mM HEPES (HyClone) pH7, 10 mM $MgCl_2$, 1 mM DTT, 0.1 mM $Na_3V_2O_4$, and 0.3 mg/ml BSA.
(2) Prepare 6H-MEK (150 nM) in KAB. Add 12 µl/well to the assay plate.
(3) Prepare ATP (66 µM) in KAB.
(4) Dilute compounds to 2.4 mM and any positive controls to 480 µM in DMSO. Perform 10-point 3× dilution in DMSO. Withdraw 2.5 µl/well of DMSO solution and add to 27.5 µl/well ATP solution in (3).
(5) Mix, then add 6 µl/well of solution in (4) to the assay plate for a DMSO concentration of 2.1% during MEK phosphorylation.
(6) Prepare c-Raf (12 nM) in KAB.
(7) Add 6 µl/well of KAB in columns 1-2 and 6 µl/well of c-Raf in columns 3-24.
(8) Incubate at 37° C. for 30 min.
(9) Prepare rabbit (α-P-(Ser 217/221)-MEK-1/2 Ab (1:240 from stock) in AB1: 50 mM HEPES pH7, 0.2 mg/ml BSA, and 43 mM EDTA.
(10) To stop reaction, add 6 µl/well of solution from (9) to the assay plate and incubate at 37° C. for 30 min.
(11) Prepare Eu-(α-rabbit IgG (9 nM) and (α-6H-SureLight-APC (120 nM) in AB2: 50 mM HEPES pH7 and 0.2 mg/ml BSA.
(12) Add 6 µl/well of solution from (11) to the assay plate.
(13) For determining the spectrum cross talk factor, prepare 2 samples following steps (1) to (10). For the blank sample, add 6 µl/well of AB2. For the cross talk factor sample, add 6 µl/well of Eu-anti rabbit IgG (9 nM).
(14) Incubate at room temperature for 1.5 hours.
(15) Read HTRF signals at 615 nm and 665 nm on the Envision. Normalize HTRF signals after spectrum cross-talk correction.

Expression and Purification of c-Raf

N terminal EE-tagged c-Raf was expressed in High-5 cells. A five liter culture was co-transfected with virus for EE-c-Raf and FLAG-vSrc at a ratio of 1:2 and harvested after 48 hours. The cell pellet was lysed in TBS containing 5 mM EDTA, 50 mM KF, 20 mM Na pyrophosphate, 20 mM β-glycerolphsphate, 0.5 mM Na $VO_3$, 1% NP-40 (w/v) and Complete Protease Tablets. The lysate was centrifuged at 20,000×g for 1 hour. The supernatant was incubated with 8 ml of anti-EE tag-Protein G Sepharose for 2 hours at 4° C. The resin was then washed with 30 volumes of the above buffer. The c-Raf protein was eluted by incubation with the above buffer containing 100 mg/ml of EE peptide for 1 hour at 4° C. Protein was concentrated using an Amicon Stir Cell with an YM10 membrane. The concentrated protein was dialyzed against TBS containing 1 mM DTT and 30% Glycerol. Protein concentration was determined by the BioRad DC method.

Purification of 6H-MEK1 (62-393)

*E. coli* cells containing the plasmid for the expression of 6H-MEK1 (62-393) were grown in Rich Media and induced with 1 mM IPTG for 24 hours at 22° C. The cell pellet was resuspent in 50 mM potassium phosphate buffer, pH 8.0, 300 mM NaCl, 5 mM $MgCl_2$, 10 mM CHAPS, 2 mM TCEP, and Complete Protease Inhibitor Tablets. Cells were disrupted by sonication. The lysate was cleared by centrifugation at 13,000×g for 45 minutes. The supernatant was diluted 1:1 with 50 mM potassium phosphate buffer, pH 8.0, 10 mM imidazole, 4 mM TCEP, 300 mM NaCl, 10 mM CHAPS, 2 mM pyrrole-2-carboxylate, and 100 mM $ZnCl_2$, then incubated with TALON metal affinity resin for 1 hour at 4° C. The resin washed with 10 volumes of 50 mM potassium phosphate buffer, pH 8.0, 5 mM imidazole, 2 mM TCEP, 300 mM NaCl, 10 mM CHAPS, 1 mM pyrrole-2-carboxylate, and 50 mM $ZnCl_2$. Proteins were eluted by incubation with 5 volumes of 20 mM HEPES, pH 8.0, 100 mM EDTA, 2 mM TCEP, 10% v/v glycerol for 1 hour at 4° C. The eluted material was concentrated using Amicon Ultra 15 devices with 10 Kd MW cutoff membranes. The sample was then subjected to size exclusion chromatography on a Superdex 200 26/60 column. The 6H-MEK1 Peak was pooled and concentrated as above. Protein was determined by the BioRad method.

b-Raf Wild-Type HTRF Assay with 6H-MEK as Substrate (Dose Response)

Assay Principle:

The assay utilizes 6H-MEK as the substrate. Upon b-Raf WT phosphorylation, phosphorylated 6H-MEK is detected with rabbit anti-phospho-MEK1/2, Eu-labeled anti-rabbit, and APC-labeled anti-6H antibodies.

Reagents and Instruments:

Enzyme: recombinant human b-Raf residues 416-end with N-terminal GST-tag from Upstate; (expressed by baculovirus in Sf21 insect cells), 0.26 mg/mL (3.87 µM assuming a molecular weight of 67.2 kD) Cat. #14-530M, Lot #25502AU, stored at −80° C.
Substrate: WT full-length 6H-MEK from C. Belunis (5126104), 4.94 mg/mL (154.4 µM assuming a MW of 32 kD) stored at −15° C.
Antibodies: Rabbit (α-P-(Ser 217/221)-MEK-1/2 Ab (from Cell Signaling, Cat. #9121B, Lot 14); Eu-(α-rabbit IgG (from Wallac, Cat. #AD0083, Lot 318663, 710 ug/mL, 4.4 µM); (α-6H-SureLight-APC (from Martek, Cat. #AD0059H, Lot E012AB01, 3.03 µM).
Reader: Envision from PerkinElmer, HTRF reading mode with 412 mirror
Assay Plate Matrix all-black polypropylene plates (Cat. #4344)
Others: Weidman 384 polypropylene plates (REMP) for compound plate.
Assay Procedure:
(1) Prepare Kinase Assay Buffer (KAB): 50 mM HEPES (HyClone) pH7, 10 mM $MgCl_2$, 1 mM DTT, 0.1 mM $Na_3V_2O_4$, and 0.3 mg/ml BSA.
(2) Prepare 6H-MEK (150 nM) in KAB. Add 12 µl/well to the assay plate.
(3) Prepare ATP (66 µM) in KAB.
(4) Dilute compounds to 2.4 mM and any positive controls to 480 µM in DMSO. Perform 10-point 3× dilution in DMSO. Withdraw 2.5 µl/well of DMSO solution and add to 27.5 µl/well ATP solution in (3).
(5) Mix, then add 6 µl/well of solution in (4) to the assay plate for a DMSO concentration of 2.1% during MEK phosphorylation.
(6) Prepare b-Raf WT (100 µM) in KAB.
(7) Add 6 µl/well of KAB in columns 1-2 and 6 µl/well of b-Raf WT in columns 3-24.
(8) Incubate at 37° C. for 30 min.

(9) Prepare rabbit (α-P-(Ser 217/221)-MEK-1/2 Ab (1:200 from stock) in AB1: 50 mM HEPES pH7, 0.2 mg/ml BSA, and 43 mM EDTA.

(10) To stop reaction, add 6 μl/well of solution from (9) to the assay plate and incubate at 37° C. for 30 min.

(11) Prepare Eu-(α-rabbit IgG (9 nM) and (α-6H-Sure-Light-APC (180 nM) in AB2: 50 mM HEPES pH7 and 0.2 mg/ml BSA.

(12) Add 6 μl/well of solution from (11) to the assay plate.

(13) For determining the spectrum cross talk factor, prepare 2 samples following steps (1) to (10). For the blank sample, add 6 μl/well of AB2. For the cross talk factor sample, add 6 μl/well of Eu-anti rabbit IgG (9 nM).

(14) Incubate at room temperature for 1.5 hours.

(15) Read HTRF signals at 615 nm and 665 nm on the Envision. Normalize HTRF signals after spectrum cross-talk correction.

b-Raf V600E Mutant HTRF Assay with 6H-MEK as Substrate (Dose Response)

Assay Principle:

The assay utilizes 6H-MEK as the substrate. Upon b-Raf V600E phosphorylation, phosphorylated 6H-MEK is detected with rabbit anti-phospho-MEK1/2, Eu-labeled anti-rabbit, and APC-labeled anti-6H antibodies.

Reagents and Instruments:

Enzyme: recombinant human b-Raf residues 416-end containing a V600E mutation with N-terminal GST-tag from Upstate; (expressed by baculovirus in Sf21 insect cells), 0.26 mg/mL (7.49 μM assuming a molecular weight of 67.3 kD) Cat. #14-5M, Lot #25633AU, stored at −80° C.

Substrate: WT full-length 6H-MEK from C. Belunis (May 26, 2004), 4.94 mg/mL (154.4 μM assuming a MW of 32 kD) stored at −15° C.

Antibodies: Rabbit (α-P-(Ser 217/221)-MEK-1/2 Ab (from Cell Signaling, Cat. #9121B, Lot 14); Eu-(α-rabbit IgG (from Wallac, Cat. # AD0083, Lot 318663, 710 ug/mL, 4.4 μM); (α-6H-SureLight-APC (from Martek, Cat. #AD0059H, Lot E012AB01, 3.03 μM).

Reader: Envision from PerkinElmer, HTRF reading mode with 412 mirror

Assay Plate Matrix all-black polypropylene plates (Cat. #4344)

Others: Weidman 384 polypropylene plates (REMP) for compound plate.

Assay Procedure:

(1) Prepare Kinase Assay Buffer (KAB): 50 mM HEPES (HyClone) pH7, 10 mM $MgCl_2$, 1 mM DTT, 0.1 mM $Na_3VO_4$, and 0.3 mg/ml BSA.

(2) Prepare 6H-MEK (150 nM) in KAB. Add 12 μl/well to the assay plate.

(3) Prepare ATP (66 μM) in KAB.

(4) Dilute compounds to 2.4 mM and positive controls to 480 μM in DMSO. Perform 10-point 3× dilution in DMSO. Withdraw 2.5 μl/well of DMSO solution and add to 27.5 μl/well ATP solution in (3).

(5) Mix, then add 6 μl/well of solution in (4) to the assay plate for a DMSO concentration of 2.1% during MEK phosphorylation.

(6) Prepare b-Raf V600E (100 μM) in KAB.

(7) Add 6 μl/well of KAB in columns 1-2 and 6 μl/well of b-Raf V600E in columns 3-24.

(8) Incubate at 37° C. for 30 min.

(9) Prepare rabbit α-P-(Ser 217/221)-MEK-1/2 Ab (1:200 from stock) in AB1: 50 mM HEPES pH7, 0.2 mg/ml BSA, and 43 mM EDTA.

(10) To stop reaction, add 6 μl/well of solution from (9) to the assay plate and incubate at 37° C. for 30 min.

(11) Prepare Eu-α-rabbit IgG (9 nM) and α-6H-SureLight-APC (180 nM) in AB2: 50 mM HEPES pH7 and 0.2 mg/ml BSA.

(12) Add 6 μl/well of solution from (11) to the assay plate.

(13) For determining the spectrum cross talk factor, prepare 2 samples following steps (1) to (10). For the blank sample, add 6 μl/well of AB2. For the cross talk factor sample, add 6 μl/well of Eu-anti rabbit IgG (9 nM).

(14) Incubate at room temperature for 1.5 hours.

(15) Read HTRF signals at 615 nm and 665 nm on the Envision. Normalize HTRF signals after spectrum cross-talk correction.

Assay Data

TABLE 1

| Kinase enzyme inhibition assay ($IC_{50}$) | | | |
|---|---|---|---|
| Example | c-Raf $IC_{50}$ (μM) | b-Raf $IC_{50}$ (μM) | b-Raf$^{V600E}$ $IC_{50}$ (μM) |
| 9 | 5.417 | 12.711 | 0.997 |
| 10 | 0.768 | 1.30 | 0.327 |
| 14 | 0.041 | 0.117 | 0.017 |
| 24 | 0.0119 | 0.045 | >50 |
| 29 | 0.231 | 0.544 | 0.094 |
| 33 | 0.341 | 1.68 | 0.258 |
| 49 | 0.017 | 5.14 | 0.92 |

What is claimed:

1. A compound of the formula

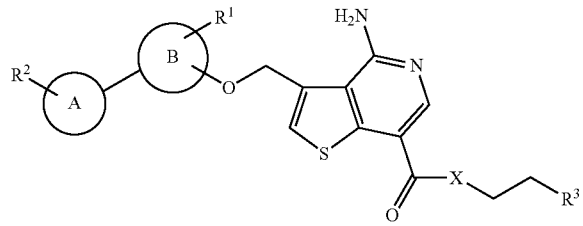

I wherein
$R^1$ is selected from the group consisting of hydrogen, lower alkyl, lower alkoxy, cyano, $NR^4R^5$, trifluoromethyl and $NO_2$;
$R^2$ is selected from the group consisting of hydrogen, lower alkyl, aryl substituted lower alkyl, lower alkoxy, substituted aryl, cyano, halogen, methyl sulfonyl, sulfonamide, trifluoromethyl, sulfonyl urea, amide, ester, carbamoyl, carbamate and urea;
$R^3$ is selected from the group consisting of hydrogen, hydroxyl, lower alkyl, lower alkoxy and $NR^4R^5$;
Ring B is aryl;
Ring A is

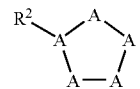

A is independently selected from C, N, O and S and Ring A is aromatic,
$R^4$ and $R^5$ are selected from hydrogen, lower alkyl or lower alkyl substituted by hydroxyl or lower alkoxy, X is O or NH,
and the pharmaceutically acceptable salts thereof.

2. The compound of claim 1 wherein $R^1$ is hydrogen or lower alkyl at the C2 of the 5-substituted 1-hydroxy ring B wherein Ring B is phenyl.

3. The compound of claim 1 wherein Ring A is selected from the group consisting of

[structures of Ring A variants with $R^2$ substituent attached to Ring B: 1,3,4-oxadiazole; 1,2,4-triazole (NH); 1,2,4-triazole (N-methyl); tetrazole; pyrazole; 1,2,4-oxadiazole; and 1,3,4-oxadiazole isomer]

wherein
$R^2$ is selected from the group consisting of hydrogen, lower alkyl, aryl substituted lower alkyl, lower alkoxy, substituted aryl, cyano, halogen, methyl sulfonyl, sulfonamide, trifluoromethyl, sulfonyl urea, amide, ester, carbamoyl, carbamate and urea and
Ring B is aryl.

4. A compound of claim 1 selected from the group consisting of
   4-Amino-3-[3-(5-methyl-[1,3,4]oxadiazol-2-yl)-phenoxymethyl]-thieno[3,2-c]pyridine-7-carboxylic acid ethyl ester;
   4-Amino-3-[3-(5-methyl-[1,3,4]oxadiazol-2-yl)-phenoxymethyl]-thieno[3,2-c]pyridine-7-carboxylic acid (2-hydroxy-ethyl)-amide,
   4-Amino-3-[2-methyl-5-(5-methyl-[1,3,4]oxadiazol-2-yl)-phenoxymethyl]-thieno[3,2-c]pyridine-7-carboxylic acid ethyl ester,
   4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide trifluoro-acetic acid salt,
   4-Amino-3-[2-methyl-5-(5-methyl-[1,3,4]oxadiazol-2-yl)-phenoxymethyl]-thieno[3,2-c]pyridine-7-carboxylic acid (2-hydroxy-ethyl)-amide toluene-4-sulfonic acid salt, and
   4-Amino-3-[2-methyl-5-(1-methyl-1H-[1,2,3]triazol-4-yl)-phenoxymethyl]-thieno[3,2-c]pyridine-7-carboxylic acid ethyl ester.

5. A compound of claim 1 selected from the group consisting of
   4-Amino-3-[2-methyl-5-(1-methyl-1H-[1,2,3]triazol-4-yl)-phenoxymethyl]-thieno[3,2-c]pyridine-7-carboxylic acid (2-hydroxy-ethyl)-amide,
   4-Amino-3-{3-[2-(4-methoxy-benzyl)-2H-tetrazol-5-yl]-phenoxymethyl}-thieno[3,2-]pyridine-7-carboxylic acid ethyl ester,
   4-Amino-3-{3-[2-(4-methoxy-benzyl)-2H-tetrazol-5-yl]-phenoxymethyl}-thieno[3,2-c]pyridine-7-carboxylic acid (2-hydroxy-ethyl)-amide,
   4-Amino-3-[3-(2-methyl-2H-tetrazol-5-yl)-phenoxymethyl]-thieno[3,2-c]pyridine-7-carboxylic acid ethyl ester,
   4-Amino-3-[3-(2-methyl-2H-tetrazol-5-yl)-phenoxymethyl]-thieno[3,2-c]pyridine-7-carboxylic acid (2-hydroxy-ethyl)-amide,
   4-Amino-3-{5-[1-(4-chloro-benzyl)-1H-[1,2,3]triazol-4-yl]-2-methyl-phenoxymethyl}-thieno[3,2-c]pyridine-7-carboxylic acid ethyl ester,
   4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide and
   4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide toluene-4-sulfonic acid salt.

6. A compound of claim 1 selected from the group consisting of
   4-Amino-3-{5-[5-(4-chloro-benzyl)-[1,3,4]oxadiazol-2-yl]-2-methyl-phenoxymethyl}-thieno[3,2-c]pyridine-7-carboxylic acid ethyl ester,
   4-Amino-3-{5-[5-(4-chloro-benzyl)-[1,3,4]oxadiazol-2-yl]-2-methyl-phenoxymethyl}-thieno[3,2-c]pyridine-7-carboxylic acid (2-hydroxy-ethyl)-amide,
   4-Amino-3-{5-[5-(4-chloro-phenyl)-[1,3,4]oxadiazol-2-yl]-2-methyl-phenoxy-methyl}-thieno[3,2-c]pyridine-7-carboxylic acid ethyl ester,
   4-Amino-3-{5-[5-(4-chloro-phenyl)-[1,3,4]oxadiazol-2-yl]-2-methyl-phenoxy-methyl}-thieno[3,2-c]pyridine-7-carboxylic acid, and
   4-Amino-3-{5-[5-(4-chloro-phenyl)-[1,3,4]oxadiazol-2-yl]-2-methyl-phenoxy-methyl}-thieno[3,2-c]pyridine-7-carboxylic acid (2-hydroxy-ethyl)-amide trifluoroacetic acid salt.

7. A compound of claim 1 selected from the group consisting of
   4-Amino-3-[2-methyl-5-(3-methyl-[1,2,4]oxadiazol-5-yl)-phenoxymethyl]-thieno[3,2-c]pyridine-7-carboxylic acid ethyl ester,
   4-Amino-3-[2-methyl-5-(3-methyl-[1,2,4]oxadiazol-5-yl)-phenoxymethyl]-thieno[3,2-c]pyridine-7-carboxylic acid,
   4-Amino-3-[2-methyl-5-(3-methyl-[1,2,4]oxadiazol-5-yl)-phenoxymethyl]-thieno-[3,2-c]pyridine-7-carboxylic acid (2-hydroxy-ethyl)-amide trifluoroacetic acid salt,
   4-Amino-3-[2-methyl-5-(5-methyl-4H-[1,2,4]triazol-3-yl)-phenoxymethyl]-thieno[3,2-c]pyridine-7-carboxylic acid ethyl ester and
   4-Amino-3-[2-methyl-5-(5-methyl-4H-[1,2,4]triazol-3-yl)-phenoxymethyl]-thieno[3,2-c]pyridine-7-carboxylic acid (2-hydroxy-ethyl)-amide.

8. A pharmaceutical composition comprising a compound of the formula

[structure of compound I: Ring A bearing $R^2$ linked to Ring B bearing $R^1$, connected via O-CH₂ to a thieno[3,2-c]pyridine core with $NH_2$ group and C(=O)-X-CH₂CH₂-$R^3$ substituent]

I wherein
- $R^1$ is selected from the group consisting of hydrogen, lower alkyl, lower alkoxy, cyano, $NR^4R^5$, trifluoromethyl and $NO_2$;
- $R^2$ is selected from the group consisting of hydrogen, lower alkyl, aryl substituted lower alkyl, lower alkoxy, substituted aryl, cyano, halogen, methyl sulfonyl, sulfonamide, trifluoromethyl, sulfonyl urea, amide, ester, carbamoyl, carbamate and urea;
- $R^3$ is selected from the group consisting of hydrogen, hydroxyl, lower alkyl, lower alkoxy and $NR^4R^5$;
- Ring B is aryl;
- Ring A is

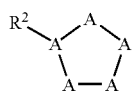

A is independently selected from C, N, O and S and Ring A is aromatic, $R^4$ and $R^5$ are selected from hydrogen, lower alkyl or lower alkyl substituted by hydroxyl or lower alkoxy, X is O or NH, or a pharmaceutically acceptable salt thereof together with a pharmaceutically acceptable carrier.

9. A compound according to claim 1 wherein $R^2$ is an aryl substituted lower alkyl and wherein said aryl is substituted by halogen or alkoxy.

10. A compound according to claim 1 wherein $R^2$ is an aryl substituted lower alkyl and wherein said aryl is substituted by halogen.

11. A compound according to claim 1 wherein said compound is 4-Amino-3-{5-[1-(4-chloro-benzyl)-1H-[1,2,3]triazol-4-yl]-2-methyl-phenoxymethyl}-thieno[3,2-c]pyridine-7-carboxylic acid (2-hydroxy-ethyl)-amide or a pharmaceutically acceptable salt thereof.

* * * * *